(12) United States Patent
Rahmouni et al.

(10) Patent No.: US 8,691,270 B2
(45) Date of Patent: *Apr. 8, 2014

(54) MISUSE PREVENTATIVE, CONTROLLED RELEASE FORMULATION

(71) Applicants: Paladin Labs Inc., Montreal (CA); Paladin Labs (Barbados) Inc., Christ Church (BB); Paladin Labs Europe Limited, Dublin (IE)

(72) Inventors: Miloud Rahmouni, Pierrefonds (CA); Angela Ferrada, Montreal (CA); Fouzia Soulhi, Dollar-des-Ormeaux (CA); Sonia Gervais, Laval (CA); Vinayak Sant, Pittsburgh, PA (US); Damon Smith, Saint-Laurent (CA); Frederic Duffayet, Montreal (CA); Shams Rustom, Saint-Laurent (CA); Ali El-Jammal, Beaconsfield (CA); Jean-Michel Ndong, Repentigny (CA); Bobby-Ernst Boursiquot, Laval (CA); Ali Bichara, Ste-Therese (CA)

(73) Assignees: Paladin Labs Inc., Montreal (Quebec) (CA); Paladin Labs (Barbados) Inc., Hastings, Christ Church (BB); Paladin Labs Europe Limited, Dublin (IE)

(*) Notice: Subject to any disclaimer, the term of this patent is extended or adjusted under 35 U.S.C. 154(b) by 0 days.

This patent is subject to a terminal disclaimer.

(21) Appl. No.: 13/919,476

(22) Filed: Jun. 17, 2013

(65) Prior Publication Data

US 2013/0344142 A1 Dec. 26, 2013

Related U.S. Application Data

(63) Continuation of application No. 12/336,495, filed on Dec. 16, 2008, now Pat. No. 8,486,448.

(60) Provisional application No. 61/014,296, filed on Dec. 17, 2007.

(51) Int. Cl.
*A61K 9/20* (2006.01)

(52) U.S. Cl.
USPC ........... 424/464; 424/465; 424/468; 424/469; 424/470

(58) Field of Classification Search
None
See application file for complete search history.

(56) References Cited

U.S. PATENT DOCUMENTS

| | | |
|---|---|---|
| 3,004,613 A | 10/1961 | Murphey et al. |
| 3,773,995 A | 11/1973 | Davies |
| 3,966,940 A | 6/1976 | Pachter et al. |
| 4,070,494 A | 1/1978 | Hoffmeister et al. |
| 4,820,522 A | 4/1989 | Radebaugh et al. |
| 4,968,509 A | 11/1990 | Radebaugh et al. |
| 5,004,613 A | 4/1991 | Radebaugh et al. |
| 5,133,974 A | 7/1992 | Paradissis et al. |
| 5,336,691 A | 8/1994 | Raffa et al. |
| 5,456,921 A | 10/1995 | Mateescu et al. |
| 5,478,577 A | 12/1995 | Sackler et al. |
| 5,591,452 A | 1/1997 | Miller et al. |
| 5,601,842 A | 2/1997 | Bartholomaeus |
| 5,603,956 A | 2/1997 | Mateescu et al. |
| 5,616,343 A | 4/1997 | Cartilier et al. |
| 5,672,360 A | 9/1997 | Sackler et al. |
| 5,681,583 A | 10/1997 | Conte et al. |
| 5,773,031 A | 6/1998 | Shah et al. |
| 6,103,261 A | 8/2000 | Chasin et al. |
| 6,156,342 A | 12/2000 | Sriwongjanya et al. |
| 6,159,501 A | 12/2000 | Skinhoj |
| 6,194,000 B1 | 2/2001 | Smith et al. |
| 6,210,714 B1 | 4/2001 | Oshlack et al. |
| 6,228,863 B1 | 5/2001 | Palermo et al. |
| 6,245,357 B1 | 6/2001 | Edgren et al. |
| 6,245,387 B1 | 6/2001 | Hayden |
| 6,254,887 B1 | 7/2001 | Miller et al. |
| 6,284,273 B1 | 9/2001 | Lenaerts et al. |
| 6,306,425 B1 | 10/2001 | Tice et al. |
| 6,309,668 B1 | 10/2001 | Bastin et al. |
| 6,326,027 B1 | 12/2001 | Miller et al. |
| 6,340,475 B2 | 1/2002 | Shell et al. |

(Continued)

FOREIGN PATENT DOCUMENTS

| | | |
|---|---|---|
| CA | 2596965 A1 | 8/2006 |
| CA | 2647360 A1 | 9/2007 |

(Continued)

OTHER PUBLICATIONS

Amabile, C.M. et al. "Overview of oral modified-release opiod products for the management of chronic pain" *Ann. Pharmacother.* 40:1327-1335 (2006).

American Pain Society, Principles of analgesic use in the treatment of acute pain and cancer pain, 4th edition. APS 1-64 (1999).

Ballantyne, J.C. et al. "Opioid therapy for chronic pain" *N. Engl. J. Med.* 349:1943-1953 (2003).

Beaulieu, A.D. et al., "A randomized, double blind, 8-week crossover study of once-daily controlled-release tramadol versus immediate-release tramadol taken as needed for chronic noncancer pain" *Clinical Therapeutics* 29:49-60 (2007).

Food and Drug Administration "FDA Asks Purdue Pharma to Withdraw Palladone for Safety Reasons" (Jul. 13, 2005) (1 page).

(Continued)

*Primary Examiner* — Hasan Ahmed
(74) *Attorney, Agent, or Firm* — Goodwin Procter LLP

(57) ABSTRACT

Disclosed is a misuse preventative, controlled release formulation comprising a core comprising a superabsorbent material (for example, polycarbophil), a controlled release coat surrounding the core, and a plurality of controlled release microparticles having a pharmaceutically active agent (for example, an opioid analgesic) disposed within the core, the coat, or both the core and the coat. When crushed, either intentionally or accidentally, and exposed to an aqueous medium, the superabsorbent material present in the core swells to encapsulate the microparticles, which remain substantially intact thereby retarding the release of the pharmaceutically active agent from the formulation. Also disclosed is a method of using the misuse preventative, controlled release formulation to deliver a pharmaceutically active agent to a mammal, for example, a human, in need thereof.

42 Claims, 14 Drawing Sheets

(56) References Cited

U.S. PATENT DOCUMENTS

| | | | |
|---|---|---|---|
| 6,372,255 B1 | 4/2002 | Saslawski et al. |
| 6,387,404 B2 | 5/2002 | Oshlack et al. |
| 6,399,096 B1 | 6/2002 | Miller et al. |
| 6,488,962 B1 | 12/2002 | Berner et al. |
| 6,607,748 B1 | 8/2003 | Lenaerts et al. |
| 6,635,280 B2 | 10/2003 | Shell et al. |
| 6,667,060 B1 | 12/2003 | Vandecruys et al. |
| 6,696,066 B2 | 2/2004 | Kaiko et al. |
| 6,696,088 B2 | 2/2004 | Oshlack et al. |
| 6,723,340 B2 | 4/2004 | Gusler et al. |
| 6,733,783 B2 | 5/2004 | Oshlack et al. |
| 6,761,895 B2 | 7/2004 | Sawada et al. |
| 6,968,551 B2 | 11/2005 | Hediger et al. |
| 7,041,320 B1 | 5/2006 | Nuwayser |
| RE39,221 E | 8/2006 | Raffa et al. |
| 7,083,807 B2 | 8/2006 | Fanara et al. |
| 7,141,250 B2 | 11/2006 | Oshlack et al. |
| 7,144,587 B2 | 12/2006 | Oshlack et al. |
| 7,157,103 B2 | 1/2007 | Sackler |
| 7,169,752 B2 | 1/2007 | Mickle et al. |
| 7,172,767 B2 | 2/2007 | Kaiko et al. |
| 7,201,920 B2 | 4/2007 | Kumar et al. |
| 7,374,781 B2 | 5/2008 | Zhang et al. |
| 7,776,314 B2 | 8/2010 | Bartholomäus et al. |
| 8,114,383 B2 | 2/2012 | Bartholomäus et al. |
| 8,309,060 B2 | 11/2012 | Bartholomäus et al. |
| 8,337,888 B2 | 12/2012 | Wright et al. |
| 8,409,616 B2 | 4/2013 | Kumar et al. |
| 8,445,018 B2 | 5/2013 | Habib et al. |
| 8,486,448 B2 * | 7/2013 | Rahmouni et al. | 424/464 |
| 8,486,449 B2 * | 7/2013 | Rahmouni et al. | 424/464 |
| 2002/0054911 A1 | 5/2002 | Oh |
| 2002/0090394 A1 | 7/2002 | Leonard et al. |
| 2002/0187192 A1 | 12/2002 | Joshi et al. |
| 2003/0004177 A1 | 1/2003 | Kao et al. |
| 2003/0031712 A1 | 2/2003 | Kaiko et al. |
| 2003/0044458 A1 | 3/2003 | Wright et al. |
| 2003/0049317 A1 | 3/2003 | Lindsay |
| 2003/0064122 A1 | 4/2003 | Goldberg et al. |
| 2003/0065002 A1 | 4/2003 | Caruso et al. |
| 2003/0068370 A1 | 4/2003 | Sackler |
| 2003/0068371 A1 | 4/2003 | Oshlack et al. |
| 2003/0068375 A1 | 4/2003 | Wright et al. |
| 2003/0068392 A1 | 4/2003 | Sackler |
| 2003/0073714 A1 | 4/2003 | Breder et al. |
| 2003/0091635 A1 | 5/2003 | Baichwal et al. |
| 2003/0092724 A1 | 5/2003 | Kao et al. |
| 2003/0118641 A1 | 6/2003 | Maloney et al. |
| 2003/0124185 A1 | 7/2003 | Oshlack et al. |
| 2003/0125347 A1 | 7/2003 | Anderson et al. |
| 2003/0143269 A1 | 7/2003 | Oshlack et al. |
| 2003/0191147 A1 | 10/2003 | Sherman et al. |
| 2004/0013726 A1 | 1/2004 | Lenaerts et al. |
| 2004/0024006 A1 | 2/2004 | Simon |
| 2004/0092542 A1 | 5/2004 | Oshlack et al. |
| 2004/0126428 A1 | 7/2004 | Hughes et al. |
| 2004/0131552 A1 | 7/2004 | Boehm |
| 2004/0131671 A1 | 7/2004 | Zhang et al. |
| 2004/0161382 A1 | 8/2004 | Yum et al. |
| 2004/0186121 A1 | 9/2004 | Oshlack et al. |
| 2004/0202716 A1 | 10/2004 | Chan et al. |
| 2004/0202717 A1 | 10/2004 | Mehta |
| 2004/0228802 A1 | 11/2004 | Chang et al. |
| 2004/0228924 A1 | 11/2004 | Oshlack et al. |
| 2005/0048115 A1 | 3/2005 | Mangena et al. |
| 2005/0063909 A1 | 3/2005 | Wright et al. |
| 2005/0095291 A1 | 5/2005 | Oshlack et al. |
| 2005/0112067 A1 | 5/2005 | Kumar et al. |
| 2005/0112195 A1 | 5/2005 | Cruz et al. |
| 2005/0158382 A1 | 7/2005 | Cruz et al. |
| 2005/0163856 A1 | 7/2005 | Maloney et al. |
| 2005/0176644 A1 | 8/2005 | Mickle et al. |
| 2005/0176645 A1 | 8/2005 | Mickle et al. |
| 2005/0191244 A1 | 9/2005 | Bartholomäus et al. |
| 2005/0192309 A1 | 9/2005 | Palermo et al. |
| 2005/0222135 A1 | 10/2005 | Buschmann et al. |
| 2005/0266070 A1 | 12/2005 | Mickle et al. |
| 2005/0276852 A1 | 12/2005 | Davis et al. |
| 2006/0002860 A1 | 1/2006 | Bartholomäus et al. |
| 2006/0009478 A1 | 1/2006 | Friedmann et al. |
| 2006/0034872 A1 | 2/2006 | Woolf |
| 2006/0058331 A1 | 3/2006 | Galer et al. |
| 2006/0073102 A1 | 4/2006 | Huaihung et al. |
| 2006/0104909 A1 | 5/2006 | Vaghefi et al. |
| 2006/0110327 A1 | 5/2006 | Emigh et al. |
| 2006/0157491 A1 | 7/2006 | Whittle et al. |
| 2006/0165602 A1 | 7/2006 | Galer et al. |
| 2006/0172006 A1 | 8/2006 | Lenaerts et al. |
| 2006/0177380 A1 | 8/2006 | Emigh et al. |
| 2006/0240107 A1 | 10/2006 | Lenaerts et al. |
| 2006/0257473 A1 | 11/2006 | Puranajoti |
| 2007/0003618 A1 | 1/2007 | Lenaerts et al. |
| 2007/0014732 A1 | 1/2007 | Sackler |
| 2007/0020188 A1 | 1/2007 | Sackler |
| 2007/0020339 A1 | 1/2007 | Bear |
| 2007/0048376 A1 | 3/2007 | Baichwal et al. |
| 2007/0060500 A1 | 3/2007 | Mickle et al. |
| 2007/0128269 A1 | 6/2007 | Gervais et al. |
| 2007/0166234 A1 | 7/2007 | Kumar et al. |
| 2007/0190142 A1 | 8/2007 | Breitenbach et al. |
| 2007/0202049 A1 | 8/2007 | Guimberteau et al. |
| 2007/0207089 A1 | 9/2007 | Abreu |
| 2007/0212414 A1 | 9/2007 | Baichwal et al. |
| 2007/0224129 A1 | 9/2007 | Guimberteau et al. |
| 2007/0231268 A1 | 10/2007 | Emigh et al. |
| 2007/0237816 A1 | 10/2007 | Finkelstein |
| 2007/0264326 A1 | 11/2007 | Guimberteau et al. |
| 2007/0264327 A1 | 11/2007 | Kumar et al. |
| 2007/0269505 A1 | 11/2007 | Flath et al. |
| 2007/0281018 A1 | 12/2007 | Qiu et al. |
| 2008/0031901 A1 | 2/2008 | Qiu et al. |
| 2008/0063725 A1 | 3/2008 | Guimberteau et al. |
| 2008/0152595 A1 | 6/2008 | Emigh et al. |
| 2008/0248113 A1 | 10/2008 | Bartholomäus et al. |
| 2008/0260844 A1 | 10/2008 | Soula et al. |
| 2009/0175937 A1 | 7/2009 | Rahmouni et al. |
| 2010/0239662 A1 | 9/2010 | Rahmouni et al. |

FOREIGN PATENT DOCUMENTS

| | | |
|---|---|---|
| EP | 0566709 A1 | 10/1993 |
| EP | 0914097 A2 | 5/1999 |
| EP | 1041987 A1 | 10/2000 |
| EP | 1389092 A1 | 2/2004 |
| EP | 1685639 A1 | 8/2006 |
| EP | 1695700 A1 | 8/2006 |
| JP | H03223211 A | 10/1991 |
| JP | 2007/254340 A | 10/2007 |
| WO | WO-99/32120 A1 | 7/1999 |
| WO | WO-01/45676 A2 | 6/2001 |
| WO | WO-01/85287 A | 11/2001 |
| WO | WO-02/092059 A1 | 11/2002 |
| WO | WO-02/092060 A1 | 11/2002 |
| WO | WO-02/094254 A2 | 11/2002 |
| WO | WO-03/013476 A1 | 2/2003 |
| WO | WO-03/013479 A1 | 2/2003 |
| WO | WO-03/013525 A1 | 2/2003 |
| WO | WO-03/013538 A1 | 2/2003 |
| WO | WO-03/026743 A2 | 4/2003 |
| WO | WO-03/039561 A1 | 5/2003 |
| WO | WO-03/094812 A1 | 11/2003 |
| WO | WO-2004/006904 A1 | 1/2004 |
| WO | WO-2004/026262 A2 | 4/2004 |
| WO | WO-2004/026283 A1 | 4/2004 |
| WO | WO-2004/041154 A2 | 5/2004 |
| WO | WO-2004/054542 A2 | 7/2004 |
| WO | WO-2004/054570 A1 | 7/2004 |
| WO | WO-2004/062614 A2 | 7/2004 |
| WO | WO-2004/091512 A2 | 10/2004 |
| WO | WO-2004/093801 A2 | 11/2004 |
| WO | WO-2005/018616 A1 | 3/2005 |
| WO | WO-2005/032555 A2 | 4/2005 |
| WO | WO-2005/053587 A1 | 6/2005 |
| WO | WO-2005/123042 A1 | 12/2005 |

(56) References Cited

FOREIGN PATENT DOCUMENTS

| WO | WO-2006/058249 A2 | 6/2006 |
|---|---|---|
| WO | WO-2006/098873 A2 | 8/2006 |
| WO | WO-2006/110642 A2 | 10/2006 |
| WO | WO-2007/013975 A2 | 2/2007 |
| WO | WO-2007/085024 A2 | 7/2007 |
| WO | WO-2008/011596 A2 | 1/2008 |
| WO | WO-2009/076764 A1 | 6/2009 |
| WO | WO-2010/069050 A1 | 6/2010 |

OTHER PUBLICATIONS

Food and Drug Administration "Information for Healthcare Professionals: Hydromorphone Hydrochloride Extended-Release Capsules (marketed as Palladone)" FDA Alert Jul. 2005 (2 pages).

Gabrielsson et al. (2002) "Multivariate methods in pharmaceutical applications," *Journal of Chemometrics*, vol. 16, pp. 141-160.

Houmes, R.J.M. et al. "Efficacy and sefety of tramadol versus morphine for moderate and severe postoperative pain with special regard to respiratory depression" *Anaesthesia and Analgesia* 74:510-514 (1992).

IPER and Written Opinion for International Application No. PCT/CA2006/002200, mailed on Apr. 22, 2009 (6 pages).

International Search Report, International Application No. PCT/CA2008/002200, mailed Apr. 22, 2009 (4 pages).

Lee, C.R. et al, "Tramadol. A preliminary review of its pharmacodynamic and pharmacokinetic properties, and therapeutic potential in acute and chronic pain states" *Drugs* 46:313-340 (1993).

Lubrizol Pharmaceutical Polymers for Controlled Release Tables and Capsules; Pharmaceutical Bulletin 30: Edition: May 31, 2011 (7 pages).

National Institue of Drug Abuse (NIDA). Commonly Abused Drugs. Updated May 19, 2010. http://www.nida.nih.gov/DrugPages/DrugsofAbuse.html (5 pages).

Pain therapeutics. Oradure Technology (http://www.durect.com/wt/durect/page-name/oradur) (2 pages) (2010).

Parrott, T. "Using opioid analgesics to manage chronic non-cancer pain in primary care" *J. Am. Board Fam. Pract.* 12:293-306 (1999).

Purdue Pharma Press release. Perdue Pharma Provides Update on Development of New Abuse-Resistant Pain Medications. Jun. 18, 2002. http://www.pharma.com/pressroom/news/oxycontinnews/20020618.htm (3 pages).

Reder, R.F. "Opioid formulations: tailoring to the needs in chronic pain" *Eur. J. Pain* 5 (suppl. A):109-111 (2001).

Resnick, R.B. et al. *Annu. Rev. Pharmacol. Toxicol.* 20:463-474 (1980).

Roberts, M. et al. "Influence of ethanol on asprin release from hypermellose matrices" *Pharmaceutics* 332:31-37.

Scott, L.J. et al. "Tramadol: a review of its use in postoperative pain" *Drugs* 60:139-176 (2000).

Spiller, H.A. et al. "Epidemiology of inhalant abuse reported to two regional poison centers" *Journal of Toxicology—Clinical Toxicology* 36:167-173 (1997).

Tiwari, S.B. et al. "Controlled release formulation of tramadol hydrochloride using hydrophilic and hydrophobic matrix system" *AAPS Pharm. Sci. Tech.* 4:1-6 (2003).

U.S. Department of Health & Human Services. Prescription Drug Abuse. Jul. 26, 2006. http://www.hhs.gov/asl/testify/t060726b.html (5 pages).

Woolf, C.J., et al. "Use and abuse of opioid analgesics: Potential method to prevent and deter non-medical consumption of prescription opioids" *Current Opinion In Investigational Drugs* 5:61-66 (2004).

Wu, W.N., et al, "Metabolism of the analgesic drug ULTRAM (tramadol hydrochloride) in humans: API-MS and MS/MS characterization of metabolites" *Xenobiotica* 32:411-425 (2002).

Wu, W.N., et al, "Metabolism of the analgesic drug, tramadol hydrochloride, in rad and dog" *Xenobiotica* 31:423-441.

Supplementary European Search Report for European Patent Application No. EP 06 861 707.1, dated Sep. 20, 2013 (7 pages).

\* cited by examiner

H₂O-RT-15 min
H₂O-50°C-15 min
H₂O-75°C-15 min
H₂O-100°C-15 min
Acidic Media-RT-15 min
Basic Media-RT-15 min
EtOH 40%-RT-15 min

US 8,691,270 B2

MISUSE PREVENTATIVE, CONTROLLED RELEASE FORMULATION

RELATED APPLICATIONS

This application is a continuation of U.S. patent application Ser. No. 12/336,495, filed Dec. 16, 2008, which claims the benefit of and priority to U.S. Provisional Patent Application Ser. No. 61/014,296, filed Dec. 17, 2007, the entire contents of each of which are incorporated by reference herein.

FIELD OF THE INVENTION

The present invention relates generally to a controlled release formulation for the delivery of at least one pharmaceutically active agent, and more specifically, the invention relates to a misuse preventative, controlled release formulation, which maintains its controlled release properties for at least one pharmaceutically active agent even when bisected or crushed and exposed to various media.

BACKGROUND OF THE INVENTION

Although significant developments have been made in the field of drug delivery, concerns remain for drugs (for example, opioid analgesics) that are subject to abuse. Furthermore, the numbers of legitimate patients misusing such drugs, either deliberately or accidentally, represents a serious medical problem. In particular, patient risk can be heightened when controlled release formulations are used because larger amounts of the pharmaceutically active agent typically are incorporated into these formulations to facilitate reduced dosing-frequency. However, while controlled release formulations may offer greater convenience and an improved adverse event profile, serious problems can occur if the control release mechanism is compromised in any way, for example, by accidental chewing or grinding of, or other damage to, the tablet, or co-ingestion with alcohol. Under these scenarios, immediate release of the pharmaceutically active agent followed by rapid absorption of up to a total daily dose of the pharmaceutical agent can have potentially fatal consequences.

While a number of approaches have been tried to address the abuse and misuse of certain drugs, no effective approach has yet been commercialized. To date, the approaches employed include, for example, deterrent formulations, agonist/antagonist formulations, and prodrug formulations.

Deterrent formulations are formulations that contain a noxious substance, such as, capsaicin, an emetic, or niacin. The aim is to prevent deliberate abuse by inflicting a painful or otherwise unpleasant reaction should the formulation be crushed or otherwise damaged prior to ingestion. For example, U.S. Patent Publication Nos. 2003/0068370, 2003/0068392 and 2007/0020188 describe incorporation of aversive agents (e.g., a bitter agent, an irritant, or an emetic agent) into a dosage containing an opioid analgesic. The aversive agents discourage an abuser from tampering with the dosage form and thereafter inhaling or injecting the tampered dosage. The potential risk of such additives to the legitimate user who accidentally damages the tablet is not addressed by such formulations.

Antagonist formulations contain inhibitors (antagonists) of the therapeutic drug. When the formulation is crushed, the inhibitors are intended to prohibit or reverse the action of the pharmaceutically active agent thereby reducing or eliminating any benefit for non-medical use. For example, naloxone is combined with pentazocine (Talwin®, sold by Sanofi-Winthrop) to deter parenteral abuse of pentazocine. Naloxone is intended to block the binding of pentazocine to opioid receptors. Similarly, naloxone is added to a buprenorphine-containing formulation (Temgesic®, sold by Reckitt & Colman). It is understood, however, that this approach can expose legitimate patients to unnecessary drugs, and can potentially inhibit effective therapy because the inhibitors may be released during normal passage through the gastrointestinal tract. These formulations also assume that effective inhibition can be achieved (i.e., that the bioavailability, pharmacokinetics and relative affinities of the agonist and antagonist can be matched so as to elicit effective inhibition in the intended recipient). U.S. Pat. Nos. 3,773,955 and 3,966,940, for example, describe formulations containing combinations of opioid agonists and antagonists, in which the antagonist does not block the therapeutic effect when the mixture is administered orally but blocks analgesia, euphoria or physical dependence when administered parenterally in a crushed form by an abuser.

Prodrug formulations rely on in vivo metabolic conversion of the prodrug into the active drug by enzymes found, for example, in the gastrointestinal tract. While these formulations may prevent euphoria via intravenous or nasal administration of the drug, they do not address the problems associated with potential intoxication (for example, alcohol intoxication) post oral administration.

Because of such limitations with existing technologies, there exists an ongoing need for misuse preventative, controlled release formulations that can reduce the risk of intentional abuse and accidental misuse of formulations containing a pharmaceutically active agent.

SUMMARY OF THE INVENTION

The invention is based, in part, upon the discovery that it is possible to create a drug delivery platform that permits the controlled release of a pharmaceutically active agent disposed within the formulation even after being sectioned (for example, bisected) or crushed. The platform is particularly useful for the administration of pharmaceutically active agents that are capable of abuse and/or that have a narrow therapeutic index. Agents capable of abuse, include, for example, analgesics (for example, opioid analgesics), hypnotic agents, anxiolytic agents, central nervous system (CNS) and respiratory stimulating agents, and agents having a narrow therapeutic index.

In one aspect, the invention provides a controlled release formulation, comprising: (a) a core comprising a superabsorbent material (for example, polycarbophil); (b) a controlled release coat surrounding the core; and (c) a plurality of controlled release microparticles having a pharmaceutically active agent disposed therein, wherein the microparticles are disposed within the core, the coat, or both the core and the coat. As a result, the formulations are designed to have two controlled release mechanisms (the coat and the microparticles), which work together in an intact formulation. However, when crushed to compromise the coating, the microparticles remain substantially intact to control the release of the pharmaceutically active agent and prevent dose dumping.

If exposed to an aqueous environment, at least one pharmaceutically active agent is released from the intact formulation over a prolonged period of time (for example, for at least 6 hours, at least 8 hours, at least 12 hours, at least 18 hours, or at least 24 hours). In certain embodiments, at least 50%, preferably 60%, more preferably 70%, and even more preferably 80% of at least one pharmaceutically active agent is prevented from being released substantially immediately (for example, within 30 minutes) from the intact formulation.

If the formulation is crushed to break the controlled release coat and expose the core, and then exposed to an aqueous environment, the superabsorbent material swells to create a hard, rigid gel that traps the microparticles, which remain substantially intact. The hard gel creates an unpleasant experience if the crushed formulation is snorted up the nose and absorbs the nasal secretions that would otherwise permit absorption via this route. Furthermore, once the hard gel has formed following exposure to an extraction media, the resulting gel cannot be pushed through a needle of a syringe. Although the controlled release properties of the coating may be compromised by crushing, the microparticles still permit the controlled release of the pharmaceutically active agent and prevent the agent from being released substantially immediately from the formulation. In certain embodiments, at least 50%, preferably 60%, more preferably 70%, and even more preferably 80% of at least one pharmaceutically active agent is prevented from being released substantially immediately (for example, within 30 minutes) from the formulation. As a result, the formulations of the invention reduce or eliminate the potential for dose dumping in water, alcohol (for example, ethanol), and other media of various pH even if the formulations have been broken or crushed.

It is understood that in certain embodiments, the controlled release microparticles can be disposed within the core or the coat. In other embodiments, the controlled release microparticles (which can be the same or different) are disposed within both the core and the coat. It is understood that the choice of location of the particles will depend upon the release profile desired for the formulation. For example, if release over 8 hours is desired, then the particles may be located within the coat. On the other hand, if release over 24 hours is desired, then the particles may be located within the core, or within both the core and the coat.

In certain embodiments, the core is monolithic. The monolithic core optionally comprises microparticles disposed therein. It is understood, however, that under certain circumstances the core can comprise a plurality of different release matrices, which can be, for example, in the form of a bilayer or a multilayer that contains two, three or more layers. In one bilayer embodiment, a first layer contains the drug containing microparticles and a second layer contains free drug (i.e., drug not present in or associated with microparticles). As a result, drug is released faster from the second layer that lacks the microparticles than from the first layer that contains the microparticles. Furthermore, it is contemplated that, depending upon the desired release profiles, one layer of the bilayer can contain one set of microparticles having one set of release kinetics and the other layer of the bilayer can contain a second, different set of microparticles having a second, different set of release kinetics.

In certain embodiments, the superabsorbent material is present such that it constitutes about 10% (w/w) to about 70% (w/w) of the core. In other embodiments, the superabsorbent material constitutes about 30% (w/w) to about 50% (w/w) of the core. In addition, relative to the intact formulation, in certain embodiments, the volume of the core constitutes about 5% to about 40% of the intact formulation, about 10% to about 30% of the intact formulation, or about 15% to about 20% of the intact formulation. In certain embodiments, the volume of the core constitutes at least 30%, at least 20%, or at least 15% of the final volume of the resulting intact formulation.

The controlled release microparticles comprise a controlled release medium (for example, cross-linked high amylose starch sold under the Tradename CONTRAMID® from Labopharm, Inc., Laval, Canada) that controls the release of the pharmaceutically active agent disposed therein and/or a controlled release coating or film. The microparticles have an average diameter in the range from about 1 µm to about 1000 µm. The microparticles, due to their small size and high radius of curvature, resist crushing when the formulation is crushed, for example, with a conventional pill crusher or between spoons or in a pestle and mortar. In one embodiment, the microparticles have an average diameter in the range from about of 200 µm to about 900 µm, or from about 300 µm to about 800 µm. The microparticles under certain circumstances have an average diameter of about 700 µm. In another embodiment, the controlled release microparticles have an average diameter in the range of from about 1 µm to about 400 µm, from about 5 µm to about 300 µm, or from about 10 µm to about 200 µm. The microparticles can have an average diameter of about 100 µm.

In addition, it is understood that the formulations can contain microparticles that contain the same pharmaceutically active agent or the same combination of two or more pharmaceutically active agents. Alternatively, the formulations can contain microparticles where one population of microparticles contain one agent and another population of microparticles contain a second, different agent.

In another aspect, the invention provides a method of providing controlled release of a pharmaceutically active agent to a mammal, for example, a human. The method comprises orally administering to an individual in need of the pharmaceutically active agent one or more of the controlled release formulations described herein.

BRIEF DESCRIPTION OF THE DRAWINGS

The foregoing and other objects, features and advantages of the invention will become apparent from the following description of preferred embodiments, as illustrated in the accompanying drawings. Like referenced elements identify common features in the corresponding drawings. The drawings are not necessarily to scale, with emphasis instead being placed on illustrating the principles of the present invention, in which.

DETAILED DESCRIPTION OF THE INVENTION

Figure 1A:
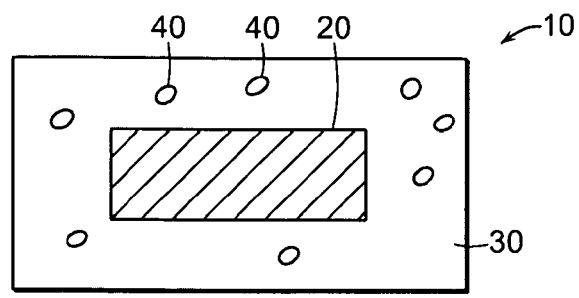
FIG. 1 shows a schematic representation of exemplary misuse preventative, controlled release formulations where controlled release microparticles containing an agent of interest are disposed within the coat (FIGS. 1A and 1D), the core (FIGS. 1B and 1E), or within both the core and the coat (FIGS. 1C and 1F), wherein, in FIGS. 1A-1C, the core is monolithic and in FIGS. 1D-1F, the core is a bilayer.

The invention is based, in part, upon the discovery that it is possible to produce a controlled release platform that provides pharmaceutical formulations less susceptible to intentional abuse and accidental misuse than other controlled release formulations and is free from noxious additives, active ingredient antagonists, prodrugs, and the like. The formulations maintain their controlled release properties when sectioned (for example, bisected) as can happen, for example, when a subject breaks a tablet in half to make it easier to swallow. Furthermore, even when crushed, the formulations of the invention prevent dose dumping because the microparticles contained within the formulation remain substantially intact and retain their controlled release properties.

The invention provides a controlled release formulation, comprising: (a) a core comprising a superabsorbent material (for example, polycarbophil); (b) a controlled release coat surrounding the core; and (c) a plurality of controlled release microparticles having a pharmaceutically active agent disposed therein, wherein the microparticles are disposed within the core, the coat, or both the core and the coat. The formulations have two controlled release mechanisms (the coat and the microparticles), which work together in an intact formulation. However, even when crushed to compromise the coating, the microparticles remain substantially intact to control the release of the pharmaceutically active agent and prevent dose dumping. As used herein, the term "dose dumping" is understood to mean an uncontrolled release of a pharmaceutically active agent where at least 80% of the pharmaceutically active agent in the formulation is released within 30 minutes (a specification that can be used to characterize a formulation as an immediate release formulation).

FIG. 1 shows certain embodiments (FIGS. 1A-1F) of the formulation of the invention. Each formulation 10 contains a core 20 and a coat 30. In FIGS. 1A and 1D, formulation 10 contains controlled release microparticles 40 located within coat 30. In FIGS. 1B and 1E, formulation 10 contains controlled release microparticles 40 located within core 20. In FIGS. 1C and 1F, formulation 10 contains controlled release microparticles 40 located within both core 20 and coat 30. In FIGS. 1A-1C, the core is monolithic. In FIGS. 1D-1F, the core is shown to be a bilayer having a first layer 50 and a second, different layer 60. It is understood, however, that the core can comprise a multilayer having two or more (for example, three, four or more) layers of different materials. In each of the embodiments shown in FIG. 1, the microparticles control the release of the active ingredient irrespective of whether the tablet is intact or compromised (for example, by bisection or crushing).

Under normal use, coat 30 protects core 20 from exposure to the solvent thereby preventing the swelling of the superabsorbent material in the core. As a result, the pharmaceutically active agent is released steadily from the formulation. If drug containing controlled release microparticles are located within coat 30, then the drug is released from coat 30 as the solvent permeates the coat. If drug containing controlled release microparticles are located within both coat 30 and core 20, then the drug initially is released from the microparticles in the coat. Over time, as the solvent gradually permeates through the coat and then accesses core 20, the drug is released from the microparticles located within the core. The formulations are designed so that coat 30 maintains sufficient integrity (for example, the coat acts like a rigid or semi-rigid net) such that the superabsorbent material in core 20 is prevented from swelling and disrupting the integrity of the tablet.

It is contemplated that the compositions described herein can be used for the delivery of one or more (for example, two, three, four or more) pharmaceutically active agents. For example, the microparticles disposed in the core can contain a first pharmaceutically active agent and microparticles disposed in the coat can contain a second, different pharmaceutically active agent. Alternatively, the microparticles disposed in the core and/or the coat can contain two or more different pharmaceutically active agents. Furthermore, it is contemplated that the core and/or the coat can comprise two or more different populations of microspheres where each population contains the same or a different pharmaceutically active agent. It is understood that the excipients present in each layer may vary. Furthermore, depending upon the release kinetics desired, a pharmaceutically active agent can be disposed in the core and/or the coat but not present within the microparticles. For example, a first pharmaceutically active agent disposed within microparticles can be present in the coat but the same or different pharmaceutically active agent not present in microparticles can be present in the core. Conversely, a first pharmaceutically active agent not present in microparticles can be present in coat but the same or different pharmaceutically active agent disposed in microparticles can be present in the core.

Figure 1B:
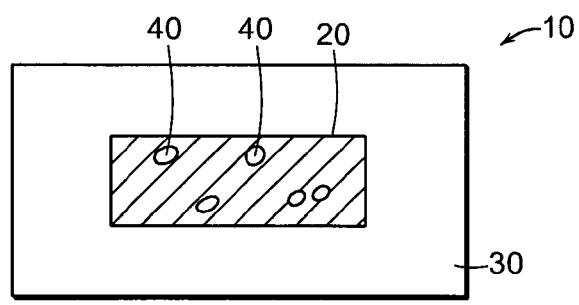
Figure 1C:
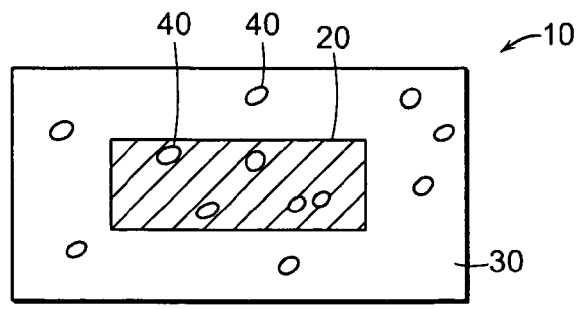
Figure 1D:
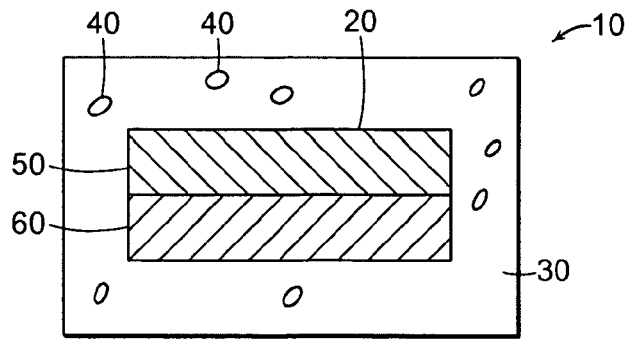
Figure 1E:
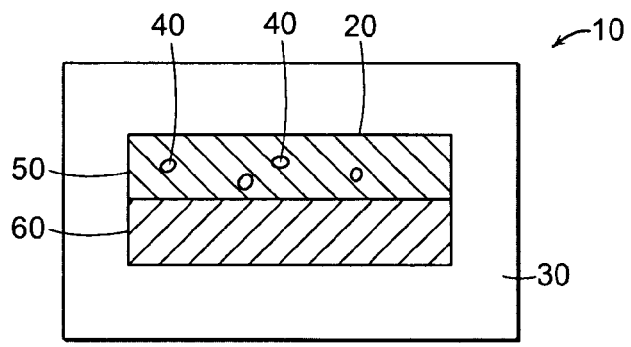

In certain embodiments, the core is monolithic (see, FIGS. 1A-1C). The monolithic core optionally can comprise microparticles disposed therein. It is understood, however, that under certain circumstances the core can comprise a plurality of different release matrices, which can be, for example, in the form of a bilayer or a multilayer that contains two, three or more layers (see, FIGS. 1D-1F). One of the layers can act can as an immediate release layer and another layer can act as a controlled release layer. Alternatively, at least two of the layers can have controlled release properties. In one embodiment, one layer can release one pharmaceutically active agent and another layer can release a different pharmaceutically active agent, which can be released at the same or at different rates. In another embodiment, one layer can release one pharmaceutically active agent at one rate and another layer can release the same pharmaceutically active agent at a different rate (i.e., faster or slower than the first layer). In one bilayer embodiment, a first layer contains drug containing microparticles and a second layer contains free drug (i.e., not contained within in or associated with microparticles). As a result, the drug is released faster from the second layer that lacks the microparticles than from the first layer that contains the microparticles. Furthermore, it is contemplated that, depending upon the desired release profiles, one layer of the bilayer can contain one population of microparticles having one set of first release kinetics and the other layer of the bilayer can contain a second, different population of microparticles having a second, different set of release kinetics.

In the case of an intact formulation, when exposed to an aqueous environment (for example, a solution containing at least 10% (v/v) water), at least one pharmaceutically active agent is released from the intact formulation over a prolonged period of time (for example, for at least 8 hours, at least 12 hours, at least 18 hours, or at least 24 hours). In certain embodiments, at least 50%, preferably 60%, more preferably 70%, and even more preferably 80% of at least one pharmaceutically active agent is prevented from being released substantially immediately (for example, within 30 minutes) from the formulation when exposed to an extraction medium, for example, water, aqueous solutions ranging in pH from 1.2 to 6.8, and different ethanolic media (for example, water containing 20% ethanol, 40% ethanol, 60% ethanol, or 80% ethanol and 100% ethanol). These features are shown, for example, in FIGS. 2-4, which are discussed in more detail in Example 2.

When the formulation is bisected, for example, axially bisected, as can happen when a patient breaks a tablet in half to make it easier to swallow, the controlled release coating becomes compromised. However, the combination of the residual coat surrounding the core, partial swelling of the core and the controlled release properties of the microparticles permit the formulations to have a release profile of the pharmaceutically active agent substantially the same as the intact tablet. Furthermore, even when bisected, the formulations of the invention permit the release of the pharmaceutically active agent over at least 12 hours, at least 18 hours, or over at least 24 hours. In certain embodiments, at least 50%, preferably 60%, more preferably 70%, and even more preferably 80% of at least one pharmaceutically active agent is prevented from being released substantially immediately (for example, within 30 minutes) from the formulation when exposed to an extraction medium, for example, water, aqueous solutions ranging in pH from 1.2 to 6.8, and different ethanolic media (for example, water containing 20% ethanol, 40% ethanol, 60% ethanol, or 80% ethanol and 100% ethanol). These features are shown, for example, in FIG. 5 and in FIG. 12.

When the formulation is crushed (for example, with a commercially available pill crusher to break formulation into at least 10 particles or more) to break the controlled release coat and expose the core, and then exposed to an aqueous environment, the superabsorbent material swells rapidly (for example, within about 30 seconds) to create a hard gel that traps the microparticles. Based in part upon their small size (high radius of curvature), the microparticles resist the crushing process and remain substantially intact. The hard gel provides an unpleasant experience if the crushed formulation is snorted up a nostril and gel formation occurs within the nostril. This process has the advantage that the nasal secretions needed for absorption of the active ingredient into the blood-stream are absorbed by the superabsorbent material preventing intoxication via this route. Similarly, if the formulation is crushed and exposed to an aqueous environment to extract the pharmaceutically active agent, the superabsorbant material in the core can absorb the extraction medium leaving little or no extraction medium to administer (see, FIGS. 6 and 7, which are discussed in Example 4). In addition, the hard gel that is formed during this process is difficult to draw or push though a syringe needle.

Although the controlled release properties of the coating are compromised by crushing, the microparticles still permit the controlled release of the pharmaceutically active agent and prevent the agent from being released substantially immediately from the formulation (i.e., the microparticles provide controlled release of the pharmaceutically active agent). For example, at least 50%, preferably 60%, more preferably 70%, and even more preferably 80% of at least one pharmaceutically active agent is prevented from being released substantially immediately (for example, within 30 minutes) from the formulation (see, FIG. 8, which is discussed in Example 4). As a result, the formulations of the invention prevent dose dumping in water, 20% ethanol, 40% ethanol, and 60% ethanol even if the formulations have been broken or crushed.

In certain embodiments, the formulation of the invention, when crushed and exposed to 900 mL of water in a U.S.P. Type I Apparatus with stirring at 100 rpm for 30 minutes at 37° C., less than about 50%, less than about 45%, less than about 40%, less than about 35%, less than about 30%, less than about 25%, or less than about 20% by weight of at least one pharmaceutically active agent originally present in the formulation before it was crushed broken is released into the water. In certain other embodiments, when the formulation of the invention is crushed and exposed to 900 mL of an aqueous solution containing 60% (v/v) ethanol in a U.S.P. Type I Apparatus with stirring at 100 rpm for 30 minutes at 37° C., less than about 50%, less than about 45%, less than about 40%, less than about 35%, less than about 30%, less than about 25%, or less than about 20% by weight of at least one pharmaceutically active agent originally present in the formulation before it was broken is released into the aqueous solution.

Each of the components of the formulation of the invention are discussed in the following sections.

A. Considerations for the Core

The core comprises a superabsorbent material, which constitutes an important feature of the invention. The term "superabsorbent material," as used herein is understood to mean any material that absorbs solvent, for example, 1 gram of material absorbs at least 30 mL, more preferably 50 mL of solvent, which, upon absorption of the solvent, swells to produce a hydrated gel (hydrogel). In general, useful superabsorbent materials, when exposed to an aqueous medium (for example, water) absorb in excess of 10-15 times, such as at least greater than 30 times, more preferably 50 times, of water based on its own weight. In certain embodiments, the superabsorbent material is a polymer.

Superabsorbent materials can be manufactured from polysaccharide derivatives or cross-linked polyelectrolytes. Polysaccharide superabsorbents include, but are not limited to, a starch graft copolymer, a crosslinked carboxymethylcellulose derivative, a cross-linked hydroxypropyl distarch phosphate, a hydrolyzed starch-acrylonitrile graft copolymer and a neutralized starch-acrylic acid graft copolymer. Cross-linked polyelectrolytes can contain functional groups such as carboxyl, sulfonate, sulphate, sulfite, phosphate, amine, imine, amide, quaternary ammonium or a mixture thereof. Examples of polyelectrolyte polymers include, but are not limited to, salts or partial salts of polyacrylic acid, polyacrylamido methylpropane sulfonic acid, polyvinyl acetic acid, polyvinyl phosphonic acid, polyvinyl sulfonic acid, an isobutylene-maleic anhydride copolymer, carboxymethyl cellulose, alginic acid, carrageenan, polyaspartic acid, polyglutamic acid, polyvinyl amine, polydiallyl dimethyl ammonium hydroxide, polyacrylamidopropyl trimethyl ammonium hydroxide, polyamino propanol vinyl ether, polyallylamine, chitosan, polylysine, polyglutamine and copolymers or mixtures thereof.

Exemplary superabsorbent materials can include a polymer selected from the group consisting of polycarbophil, polycarbophilic calcium, polymethacrylic acid, polyacrylic acid, and mixtures thereof. Polycarbophil is a superabsorbent polymer is capable of absorbing and retaining large quantities of water. Polycarbophil is a high molecular weight acrylic acid polymer cross-linked with divinyl glycol, and is sold under the tradename, NOVEON® AA-1, by Lubrizol Corporation OH, USA. It is understood that 1 gram of polycarbophil can absorb about 62 grams of water. Polycarbophil is stable and does not undergo hydrolysis or oxidation under normal conditions. Calcium salts of polycarbophil (polycarbophilic calcium) can be used and are available commercially under the tradename NOVEON® CA-1 or CA-2 from Lubrizol Corporation OH, USA. Other exemplary superabsorbent materials include Carbopol® polymers, which are acrylic acid polymers cross-linked with, for example, allyl ethers of pentaerythritol, for example, Carbopol® 71G (a carbomer homopolymer type A), Carbopol® 971P (a carbomer homopolymer type A), and Carbopol® 974 (a carbomer homopolymer type B), each of which is available from Lubrizol Corporation, OH, USA.

The superabsorbent material provides two functions. First, when the formulation containing the superabsorbent material (for example, polycarbophil) is crushed and combined with solvent (for example, water) for parenteral injection, the superabsorbent material rapidly absorbs the water, swells and forms a hard gel thus preventing injection. In addition, depending upon the amount of solvent added, all of the solvent may be absorbed leaving no residual solvent that can be administered. Second, if the formulation is crushed and snorted into a nostril the superabsorbent material absorbs the liquid in the nostril causing the superabsorbent material to swell. Not only does the swelling cause discomfort but also prevents the drug disposed within the formulation from being rapidly released (for example, within less than 30 minutes).

In general, the proportion of the superabsorbent material in the core varies from about 10% (w/w) to about 70% (w/w) of the core, more preferably from about 30% (w/w) to about 50% (w/w) of the core. Furthermore, the superabsorbent material in the core varies from about 2% (w/w) to about 20% (w/w) of the final intact formulation, more preferably from about 4% to about 14% of the final intact formulation, more preferably from about 6% to about 12% of the final intact formulation.

In addition, relative to the intact formulation, the volume of the core constitutes from about 5% to about 40% of the intact formulation, from about 10% to about 30% of the intact formulation, or from about 15% to about 20% of the intact formulation. In certain embodiments, the volume of the core constitutes at least 30%, at least 20%, or at least 15% of the final volume of the resulting intact formulation.

In addition to the superabsorbent material, the core can comprise other excipients and manufacturing aids including, for example, one or more of granulation aids (for example, xanthan gum, polyethylene oxide, polyvinylpyrollidone, cellulose and sucrose derivatives, and mixtures thereof), a lubricant (for example, magnesium stearyl fumarate, magnesium stearate, and stearic acid), a glidant (for example, colloidal silicon dioxide and talc), a dye (for example, iron oxide), and a filler (for example, microcrystalline starch).

In addition, the core can comprise controlled release microparticles containing a pharmaceutically active agent of interest. Compositions of exemplary controlled release microparticles and methods for their manufacture are described in Section C below.

In certain embodiments, the core is monolithic, and optionally comprises microparticles disposed therein. It is understood, however, that under certain circumstances the core can comprise a plurality of different release matrices, which can be, for example, in the form of a bilayer or a multilayer that contains two, three or more layers. One of the layers can act can as an immediate release layer and another layer can act as a controlled release layer. Alternatively, at least two of the layers can have controlled release properties. In one embodiment, one layer can release one pharmaceutically active agent and another layer can release a different pharmaceutically active agent, which can be released at the same or at different rates. In another embodiment, one layer can release one pharmaceutically active agent at one rate and another layer can release the same pharmaceutically active agent at a different rate (i.e., faster or slower than the first layer).

B. Considerations for the Coat The coat, when present, performs an important function in the operation of the formulation of the invention. The coat provides a hard outer shell that (i) resists damage by crushing or chewing, (ii) resists the release of drug as the pH of the extraction media varies (for example, when the formulations are combined with conventional carbonated beverages), (iii) resists the release of drug in the presence of alcohol in the extraction media even at levels that exceed the alcohol content of alcoholic beverages, and (iv) permits permeation by solvent to permit the release of drug disposed within microparticles located in the core and/or the coat. Under normal use, the coat still provides a rigid net-like structure that encapsulates the core and prevents the superabsorbent material in the core from swelling.

In certain embodiments, the coat comprises a controlled release agent. Alternatively, or in addition, the coat is a controlled release coating. Exemplary controlled release agents and coatings can be selected from the group consisting of acetate succinate, a polyvinyl derivative (for example, polyvinyl alcohol, polyvinyl acetate, polyvinyl acetate phthalate, a copolymer of vinyl acetate and vinyl pyrrolidone, a copolymer of vinyl acetate and crotonic acid, polyvinylpyrollidone), polyethylene oxide, polyacrylic acid, polysaccharides (for example, modified starch, cross-linked high amylose starch, hydroxypropyl starch, hydroxypropyl methylcellulose phthalate, cellulose and cellulose derivatives (for example, microcrystalline cellulose, carboxymethylethyl cellulose, cellulose acetate, methylcellulose, ethylcellulose, hydroxypropyl cellulose, hydroxypropylmethyl cellulose, cellulose phthalate, cellulose acetate, cellulose acetate phthalate, cellulose acetate propionate, cellulose-acetate succinate, cellulose acetate butyrate, cellulose-acetate trimellitate)), poloxamer, povidone, alginic acid, sodium alginate, polyethylene glycol, polyethylene glycol alginate, gums (for example, xanthan gum), polymethacrylates (including, for example, a copolymer of methacrylic acid and methyl-methacrylate, and a copolymer of methacrylic acid and ethyl acrylate), a copolymer of methacrylic acid and ethyl acrylate, a copolymer of polymethyl vinyl ether and malonic acid anhydride, a copolymer of polymethyl vinyl ether and malonic acid or the ethyl-, isopropyl-, n-butylesters thereof, zein, and mixtures of the foregoing.

Further examples of controlled release film-coating polymers include, but are not limited to, methylcellulose, ethylcellulose (for example, Aquacoat® type from FMC Corp.), methylhydroxyethylcellulose, methylhydroxypropylcellulose (for example, Pharmacoat® type from Shin Etsu Corp.), ethylhydroxyethylcellulose, hydroxyethylcellulose, hydroxypropylcellulose, carboxymethylcellulose or methylcarboxymethylcellulose, acrylic polymers, polyvinylacetates, polyvinyl chlorides, polymethylmetacrylates or a terpolymer of vinylchloride, vinylalcohol and vinylacetate, hydroxypropylmethylcellulose phthalate (for example, HP type from Shin Etsu), hydroxypropylmethylcellulose acetate succinate (for example, Aqoat from Shin Etsu), cellulose acetate phthalate (for example, Aquacoat CPD from FMC Corp. or C-A-P NF from Eastman Chemical), polyvinyl acetate phthalate (for example, Sureteric from Colorcon), carboxymethylethylcellulose, and co-polymerized methacrylic acid/methacrylic acid methyl esters (for example, Eudragit from Degussa/Evonik Industries or Kollicoat from BASF or Acryl-Eze from Colorcon or Eastacryl from Eastman Chemical).

In one embodiment, Kollidon® SR (a powder consisting of polyvinyl acetate (8 parts, w/w) and polyvinyl pyrrolidone (2 parts, w/w)) is used in combination with xanthan gum. Kollidon® SR is available from BASF, ON, Canada. In another embodiment, the coat can be, for example, Eudragit® L30D 55, available from Degussa/Evonik Industries, NJ, USA. Furthermore, it is understood that, depending upon the release kinetics desired, the same controlled release agents and coatings can be disposed within or can coat the microparticles described below in Section C.

In addition, the coat can comprise one or more of a viscosity increasing agent (for example, xanthan gum, polyethylene oxide, polyvinylpyrollidone, cellulose and sucrose derivatives), a lubricant (for example, sodium stearyl fumarate, magnesium stearate and stearic acid), a glidant (for example, colloidal silicon dioxide and talc), and a dye (for example, iron oxide).

In some embodiments, the coat may comprise a plasticizer. Examples of plasticizers include, but are not limited to, cetanol, triacetin, citric acid esters, phthalic acid esters, dibutyl succinate, acetylated monoglyceride, acetyltributyl, acetyltributyl citrate, acetyltriethyl citrate, benzyl benzoate, calcium stearate, castor oil, cetanol, chlorebutanol, colloidal silica dioxide, dibutyl phthalate, dibutyl sebacate, diethyl oxalate, diethyl malate, diethyl maleate, diethyl malonate, diethyl fumarate, diethyl phthalate, diethyl sebacate, diethyl succinate, dimethylphthalate, dioctyl phthalate, glycerin, glyceroltributyrate, glyceroltriacetate, glyceryl behanate, glyceryl monostearate, hydrogenated vegetable oil, lecithin, leucine, magnesium silicate, magnesium stearate, polyethylene glycol, propylene, glycol, polysorbate, silicone, stearic acid, talc, titanium dioxide, triacetin, tributyl citrate, triethyl citrate, zinc stearate, PEG (polyethylene glycol), and the like.

In one embodiment, the coat contains Kollidon® SR and xanthan gum as release controlling agents, colloidal silicon dioxide as a glidant, and sodium stearyl fumarate as a lubricant. Incorporation of Kollidon® SR and xanthan gum into the coat helps provide a controlled-release of the pharmaceutically active agent (for example, tramadol HCl), and significantly increases the mechanical strength of the resulting formulations making them harder to crush.

In addition, the coat can comprise controlled release microparticles containing a pharmaceutically active agent of interest. Compositions of exemplary controlled release microparticles and methods for their manufacture are described in the following section.

C. Considerations for the Controlled Release Microparticles

Figure 1F:
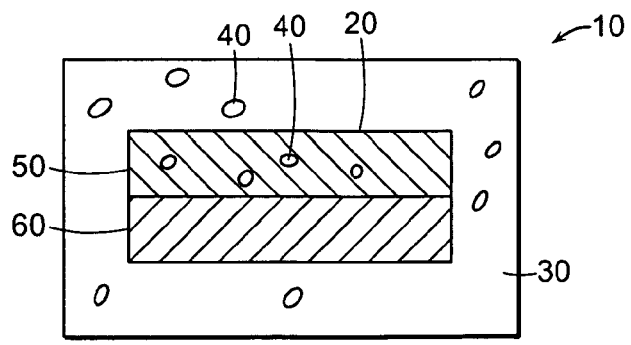

As shown in FIG. 1, the formulations of the invention comprises controlled release microparticles disposed within the coat (FIGS. 1A and 1D), the core (FIGS. 1B and 1E), or within both the core and the coat (FIGS. 1C and 1F). The controlled release microparticles contain pharmaceutically active agent and facilitate the controlled release of the pharmaceutically active agent disposed therein. Depending upon the configuration chosen, the formulations can release the pharmaceutically active agent over a prolonged period of time, for example, at least 6 hours, at least 8 hours, at least 12 hours, at least 18 hours, or at least 24 hours.

Although the controlled release particles may take a variety of forms, they have a number of features in common, which include (i) they have controlled release properties and (ii) they are of a size that makes them hard to crush even when the formulations are crushed with a conventional pill crusher. The microparticles may have a core and a coat, where either or both provide controlled release properties.

The core of the microparticles can comprise the pharmaceutically active agent and a variety of excipients, which include, for example, one or more of, a spheronizing agent, a plasticizer, and a controlled release agent. Exemplary spheronizing agents include, for example, microcrystalline cellulose, ethyl cellulose, low substituted hydroxypropylcellulose and dicalcium phosphate dihydrate. Microcrystalline cellulose is preferred and is available commercially under the tradename Avicel® PH101 from FMC BioPolymer, DE, USA. Microcrystalline cellulose forms a plastic and cohesive mass upon wetting, which is desirable for the successful production of spherical granules. Microcrystalline cellulose is considered to aid the spheronization process by absorbing water like a molecular sponge and helps in the binding and lubrication of the moistened powder mass during extrusion. During the spheronization process, moisture trapped in the microcrystalline cellulose microfibrils adds plasticity to the extrudate and helps convert short round extrudates obtained by extrusion into spherical pellets. Different grades of microcrystalline cellulose are commercially available, and a preferred grade suitable for extrusion-spheronization is Avicel® PH 101, because of its small particle size, low packing density and high water retentive capacity.

In addition, the core of the microparticles can contain a plasticizer. Exemplary plasticizers include, for example, Plasacryl available from IMTech, PA, USA, and triethyl citrate available from Morflex, NC, USA.

In addition, the core of the microparticles optionally can contain a controlled release agent that controls the release of the pharmaceutically active agent. Exemplary controlled release agents can be selected from the group consisting of starch, starch derivatives, cellulose derivatives, xanthan gum, polyethylene glycol, polyvinyl acetate, polyvinyl alcohol, and mixtures thereof. In a preferred embodiment, the controlled release excipient includes a starch derivative that is a cross-linked high amylose starch, which provides the controlled release of the pharmaceutically active agent for at least 12 hours, for at least 18 hours, or for at least 24 hours. The cross-linked high amylose starch can be cross-linked with phosphorus oxychloride and/or can contain hydroxypropyl side chains. In certain embodiments, a suitable controlled release agent is commercially available from Labopharm, Inc., Laval, Canada, under the trademark CONTRAMID®. The synthesis of the CONTRAMID® excipient is described in U.S. Pat. No. 6,607,748.

The core of the microparticles containing a pharmaceutically active agent can be prepared by a variety of methods, including, for example, wet granulation and extrusion-spheronization. During wet granulation, microparticles are prepared using, for example, a fluid bed rotor granulator. The wet granulation process comprises, for example, (i) wetting the powder to form wet granules; (ii) exposing the wet granules to tumbling or spheronization, and (iii) drying the product of step (ii). Alternatively, the pellets can be produced by extrusion-spheronization, which has the advantage of being highly reproducible, easy to scale up, cost effective, and produces substantially perfect spherical microparticles. Extrusion-spheronization comprises, for example, (i) wetting the powder blend with an aqueous or organic solution generally containing a binder to form a wet homogeneous mass suitable for wet extrusion, (ii) extruding the wet mass to form cylindrical extrudates of uniform shape and size, and (iii) spheronizing the wet extrudates using a spheronizer, where, for example, a fast spinning disc, breaks the extrudates into smaller microparticles and rounds them to form spheres.

The cores of the microparticles can be coated with a controlled-release coating that is sufficiently flexible to be deformed under compression during tablet formation without undergoing fracture. Suitable controlled release agents are described in the previous section. In one embodiment, the controlled release coating comprises polymethacrylate (e.g., Eudragit® RS, available from Degussa/Evonik Industries, NJ, USA). Eudragit® RS30D grade, which is particularly useful is an aqueous dispersion (30% w/w) of a polymeric mixture of ethyl acrylate, methyl methacrylate, and trimethylammonioethyl methacrylate at a ratio of 1:2:0.1 (w/w). The Eudragit® RS grade is designed to form water-insoluble film coats for sustained release formulations. The Eudragit® RS grade forms a highly flexible film coat with low permeability. Another useful coating material includes Eudagrit® L30D 55, available from Degussa/Evonik Industries, NJ, USA. Another controlled release coating comprises ethyl cellulose sold under the tradename Surelease®. Another controlled release coating includes Kollicoat SR, available from BASF Fine Chemicals. In one approach, the core of the microparticles is coated using a fluid bed coater equipped with a bottom spray.

The resulting particles, depending upon their composition and method of fabrication have an average diameter in the range of from about 1 μm to about 1000 μm. In certain embodiments, the microparticles have an average diameter of from about of 200 μm to about 900 μm, or from about 300 μm to about 800 μm. In certain embodiments, the resulting microparticles have an average diameter of about 700 μm. In certain other embodiments the microparticles have an average diameter of from about 1 μm to about 400 μm, from about of 5 μm to about 300 μm, or from about 10 μm to about 200 μm. In certain embodiments, the resulting microparticles have an average diameter of about 100 μm.

D. Pharmaceutically Active Agents

It is understood that the compositions described herein can be used for the delivery of one or more pharmaceutically active agents. In certain embodiments, the controlled release microparticles can contain one or more pharmaceutically active agents. In addition, it is understood that the formulations of the invention can contain a number of different microparticles, with one population of microparticles containing one pharmaceutically active agent and another population of microparticles containing a second, different pharmaceutically active agent.

Many pharmaceutically active agents can benefit from being delivered using the formulations described herein. The Controlled Substances Act (CSA), Title II of the Comprehensive Drug Abuse Prevention and Control Act of 1970, places all substances that are regulated under existing Federal Law into one of five schedules based upon the substance's medicinal value, harmfulness, and potential for abuse or addiction. The formulations of the invention are preferably used to deliver those drugs classified as Schedule II, III, IV and V drugs. Similarly, although any drug in which there is a benefit in having controlled release of the drug can be incorporated into formulations of the invention, the formulations described herein are particularly useful in the delivery of, for example, CNS and respiratory stimulant agents, analgesics (for example, opioid analgesics), hypnotic agents, anxiolytic agents, and agents with a narrow therapeutic index. For purposes of this invention, pharmaceutically active agents are intended to encompass salts, esters, and the prodrugs of the pharmaceutically active agents.

Exemplary opioid analgesics include, for example, alfentanil, buprenorphine, butorphanol, carefentanil, codeine, dezocine, diacetylmorphine, dihydrocodeine, dihydromorphine, diprenorphine, etorphine, fentanyl, hydrocodone, hydromorphone, β-hydroxy-3-methylfentanyl, levo α-acetylmethadol, levorphanol, lofentanil, meperidine, methadone, morphine, nalbuphine, oxycodone, oxymorphone, pentazocine, pethidine, propoxyphene, remifentanil, sufentanil, tilidine, tramadol hydrochloride, or a mixture thereof.

Exemplary hypnotics include, for example, benzodiazepines and non-benzodiazepines. Exemplary benzodiazepines include, but are not limited to, alprazolam, diazepam, flurazepam, loprazolam mexazolam, nitrazepam, and the like. Exemplary non-benzodiazepines include, but are not limited to, barbiturates (for example, butobarbitone, phenobarbitone, or amylobarbitone) chlormethiazole, eszopiclone, ramelteon, zaleplon, zopiclone, zolpidem, and the like.

Exemplary anxiolytic agents include, but are not limited to, amphetamine, buspirone, barbiturates, benzodiazepines (for example, alprazolan, bromazepam, brotizolam, camazepam, chlordiazepoxide, clobazam, clonazepam, desalkylflurazepam, diazepam, flunitrazepam, flurazepam, lorazepam, lometazepam, medazepam, metaclazepam, midazolam, nitrazepam, nordazepam, oxazepam, pentylenetetrazole, prazepam, temazepam, tetrazepam, and triazolam) and the like.

Exemplary CNS and respiratory stimulatory agents include, but are not limited to xanthines (for example, caffeine and theophylline), amphetamines (for example, amphetamine, benzphetamine hydrochloride, dextroamphetamine, dextroamphetamine sulfate, levamphetamine, levamphetamine hydrochloride, methamphetamine, and methamphetamine hydrochloride), and miscellaneous stimulants such as methylphenidate, methylphenidate hydrochloride, modafinil, pemoline, sibutramine, and sibutramine hydrochloride.

Pharmaceutically active agents with a narrow therapeutic index include, for example, amiodarone, amphotericin, cabamazepine, clozapine, digoxin, disopyramide, lithium carbonate, minoxidil, phenyloin, primidone, procainamide, quinidine, theophylline, valproic acid, and warfarin.

It will be appreciated that the amount of the pharmaceutically active agent present in the abuse-resistant formulation depends upon the therapeutic dose required in conventional tablets. In generally, each pharmaceutically active agent is present in an amount ranging from about 0.5 mg to about 900 mg by weight, from about 1 mg to about 700 mg by weight, from about 1 mg to about 600 mg by weight, from about 1 mg to about 500 mg, from about 1 mg to about 400 mg, from about 1 mg to about 300 mg, from about 1 mg to about 200 mg, and from about 10 mg to about 200 mg. It is understood, however, that the actual dosage will depend upon the particular pharmaceutically active ingredient and its proposed use.

The invention also provides a solid dosage form for the controlled release of a pharmaceutically active agent disposed therein. The solid dosage form comprises an admixture of a superabsorbent material (for example, polycarbophil) and a plurality of controlled release microparticles having a pharmaceutically active agent disposed therein. When the solid dosage form is exposed intact to an aqueous environment, the pharmaceutically active agent is released from the solid dosage form over a prolonged period of time. However, when the solid dosage form is crushed to expose the interior of the core and exposed to an aqueous environment, the superabsorbent material swells to create a hard gel that traps the microparticles, and the microparticles provide controlled release of the pharmaceutically active agent. The solid dosage form can be coated or uncoated. Accordingly, it is understood that the features and components of the coated formulations described hereinabove are also applicable to the solid dosage form.

It is understood that the intact compositions described herein can be produced using techniques known to those in a formulary arts. An exemplary protocol for producing controlled release tablets is described in Example 1. It is understood, however, that other approaches can be used to make formulations of the invention. The formulations of the invention preferably have a hardness in the range of from about 100 N to about 500 N, or from about 150 N to about 400N, or from about 200 N to about 400N, or from about 300 N to about 400 N, with a target hardness of at least 200 N. Furthermore, the formulations of the invention may take the form of capsules, caplets, tablets, or pills.

The formulations of the invention can be used to administer a pharmaceutically active agent to a mammal, for example, a human, in need of the pharmaceutically active agent (for example, an opioid analgesic for pain management). It is understood that the exact dosage will vary depending on the symptoms, age, body weight, severity of the disease to be treated and can be optimized through routine experimentation known to those of skill in the art.

EXAMPLES

Practice of the invention will be more fully understood from the foregoing examples, which are presented herein for illustrative purposes only, and should not be construed as limiting the invention in any way.

Example 1

Preparation of Exemplary Tramadol Containing Controlled Release Formulation

This Example describes an exemplary misuse preventative tablet and how it can be made. The formulation contains tramadol, an opioid drug used for the treatment of moderate to moderately severe pain, which is capable of being abused and for which over exposure via misuse can lead to harmful side effects. The misuse preventative tablet described in this Example contains 100 mg of tramadol HCl which, as can be seen from Example 2, is released from the intact tablets over 24 hours The formulation of the complete tablet is set forth in Table 1, and the manufacture of each of the components for the formulation appear in the following sections of this Example.

TABLE 1

| | Mg/Tablet | |
| --- | --- | --- |
| Component | Core blend | Coat blend |
| Tramadol HCl | 25.0 | 75.0 |
| Avicel PH 101 | 30.6 | 30.0 |
| Contramid | 0.7 | 2.1 |
| Polycarbophil (Noveon AA-1) | 62.9 | — |
| Xanthan gum | 20.6 | 241.6 |
| Kollidon SR | — | 120.5 |
| Eudragit RS 30 D | 5.7 | 17.1 |
| Triethyl citrate | 0.6 | 1.7 |
| Plasacryl | 0.9 | 2.6 |
| Colloidal silicon dioxide | 0.75 | 2.5 |
| Sodium stearyl fumarate | 1.5 | 5.0 |

TABLE 1-continued

| | Mg/Tablet | |
|---|---|---|
| Component | Core blend | Coat blend |
| FD&C Blue #1 Aluminium lake 11-13 | 0.08 | — |
| Opadry white | 0.67 | 21.3 |

The formulation of Table 1 was prepared by a multi-step process, which is outlined below in subsections A-D.

A. Manufacture of Tramadol Containing Controlled Release Microparticles

The formulation of uncoated microparticles is set forth in Table 2, and the uncoated microparticles were produced as follows. The various components were mixed in a mixer for 3 minutes under low shear conditions. The dry blend then was wetted under agitation in the same mixer by gradually adding water until a homogeneous wet mass suitable for extrusion was produced. The wet mass then was extruded at a constant speed (45 rpm) using a Laboratory Multigranulator extruder model MG-55 from LCI, Inc., NC, USA equipped with a dome die having a 0.6 mm diameter hole and a fixed extrusion gap. The extrudes then were spheronized at a constant speed (1800 rpm) using a Marumerzier Model QJ-230T from LCI, Inc., NC, USA. The wet microparticles were dried at 45° C. in a fluid bed until a moisture content of about 2% was achieved.

TABLE 2

| Components | % by Weight in Uncoated Microparticles | Weight (g) in Batch |
|---|---|---|
| Tramadol HCl | 70.0 | 2,800.0 |
| Avicel PH-101 | 28.0 | 1,120.0 |
| Contramid | 2.0 | 80.0 |
| Water | — | 600.0 |
| Total | 100.0 | 4000.0 |

The resulting microparticles then were coated with a controlled release coating and an Opadry II White containing film as described in Table 3. The microparticles were coated in a fluid bed coater. The microparticles were film coated to a weight gain of between 7% and 15% using an aqueous solution of Eudragid RS30C containing Plasacryl and triethyl citrate (TEC). Afterwards, a curing solution containing Opadry II White was added to provide a film around the Eudragit containing coat to reduce the likelihood of the microparticles sticking together.

TABLE 3

| Coating Solution for Microparticles | | |
|---|---|---|
| Components | Dry substance (g) | Quantity weighed (g) |
| Uncoated pellets | — | 1000.0 |
| Eudragit RS 30 D | 160.0 | 533.3 |
| TEC | 24.0 | 24.0 |
| Plasacryl | 16.0 | 80.0 |
| Curing Solution for Microparticles | | |
| Opadry II White | 18.0 | 18.0 |

The resulting controlled released microparticles had a mean diameter of about 700 μm as measured by an optical microscope.

B. Manufacture of Core Composition

In addition to the controlled release microparticles, the core contained polycarbophil as well as several other components. The remaining excipients for the core are set forth in Table 4, and were mixed and subjected dry granulation in a roller compactor (Vector Corp.) under a roll speed of 5 rpm, a screw speed of 19 rpm, and a pressure of 800 psi.

TABLE 4

| Components | % by Weight in Core Granulation | Quantity Weighed (g) |
|---|---|---|
| Polycarbophil | 59.80 | 1794.0 |
| Avicel PH-101 | 19.85 | 595.5 |
| Xanthan Gum | 19.85 | 595.5 |
| Colloidal silicon dioxide | 0.25 | 7.5 |
| Sodium stearyl fumarate | 0.25 | 7.5 |
| Total | 100.0 | 3000.0 |

The tramadol containing microparticles then were mixed with the remaining granulated core excipients to produce the formulation of the core, which is set forth in Table 5.

TABLE 5

| | | Formulation Composition | | |
|---|---|---|---|---|
| Core Blend | | Mg/ Tablet | Granulation (mg) | % of Core | g/batch |
| Tramadol Containing Microparticles | | 43.5 | | 29.00 | 464.0 |
| Granulated Excipients | Polycarbophil | 104.7 | 62.58 | 69.79 | 1116.6 |
| | Xanthan gum | | 20.72 | | |
| | Avicel PH 101 | | 20.82 | | |
| | Colloidal silicon dioxide | | 0.26 | | |
| | Sodium stearyl fumarate | | 0.26 | | |
| Colloidal silicon dioxide | | 0.5 | | 0.33 | 5.3 |
| Sodium stearyl fumarate | | 1.2 | | 0.83 | 13.3 |
| FD&C Blue #1 Aluminium Lake 11-13 | | 0.1 | | 0.05 | 0.8 |
| Total | | 150.0 | | 100.00 | 1600 |

C. Manufacture of Coat Composition

In addition to the controlled release microparticles, the coat contained Kollidon® SR and xanthan gum as well as several other components. The remaining excipients for the coat are set forth in Table 6, and were mixed and subjected to dry granulation in a roller compactor (Vector Corp.) under a roll speed of 5 rpm, a screw speed of 19 rpm, and a pressure of 800 psi.

TABLE 6

| Components | % by Weight in Coat Granulation | Quantity Weighed (g) |
|---|---|---|
| Crospovidone (Kollidon® SR) | 33.17 | 995.1 |
| Xanthan gum | 66.33 | 1989.9 |
| Colloidal silicon dioxide | 0.25 | 7.5 |
| Sodium stearyl fumarate | 0.25 | 7.5 |
| Total | 100.00 | 3000.0 |

The tramadol containing microparticles then were mixed with the remaining granulated coat excipients to produce the formulation of the coat, which is set forth in Table 7.

TABLE 7

| Coat blend | | Mg/tablet | Granulation (Mg) | % of Coat | g/batch |
|---|---|---|---|---|---|
| Tramadol Containing Microparticles | | 130.5 | | 26.10 | 1409.4 |
| Granulated Excipients | Kollidon ® SR | 363.8 | 120.46 | 72.75 | 3928.3 |
| | Xanthan gum | | 240.88 | | |
| | Colloidal silicon dioxide | | 0.91 | | |
| | Sodium stearyl fumarate | | 0.91 | | |
| Colloidal silicon dioxide | | 1.6 | | 0.32 | 17.3 |
| Sodium stearyl fumarate | | 4.2 | | 0.83 | 44.9 |
| Total | | 500.0 | | 100.00 | 5400.0 |

D. Tablet Manufacture

Dry-coated tablets then were prepared using a Dry-Cota 16-Station tablet press from Manesty, UK. The core formulation was added to a first hopper in the tablet press and compressed into a core tablet. The coat formulation then was added to a second hopper in the tablet press and the core and the coat were compressed together to form the dry coated tablet. The resulting dry coated tablets then were film coated with a solution of Opadry II using a fully perforated pan coating machine (O'Hara, Mississauga, ON, CA). The formulation of film coated tablets is set forth in Table 8.

TABLE 8

| Components | Quantity weighed (g) |
|---|---|
| Dry Coated Tablets | 2000.0 |
| Opadry II White solution (20%) | 60.0 |

The resulting tablets had a hardness in the range of from about 300 N to about 400 N. with a target hardness of about 350 N.

Example 2

Release Properties of Intact Tablets

The release kinetics of the intact tablets produced in Example 1 were studied in this Example. In addition, the release kinetics were studied when alcohol was included in the extraction media and also when the pH of the extraction media was varied.

Initially, tramadol release was measured using the rotating basket method (U.S.P. Type I Apparatus) as described in U.S.P. 30 at 100 rounds per minute, at 37±0.5° C., in 900 mL of potassium phosphate monobasic pH 6.8 solution (buffer stage) during 24 hours. The results from three experiments are summarized in FIG. 2. As can be seen from FIG. 2, the tablets produced in Example 1 release tramadol over a 24 hour period with kinetics summarized in Table 9.

TABLE 9

| Time (hours) | % Tramadol Release | Standard Deviation |
|---|---|---|
| 0.5 | 4 | 0.4 |
| 1.0 | 8 | 0.7 |
| 2.0 | 17 | 1.6 |
| 4.0 | 31 | 2.6 |

TABLE 9-continued

| Time (hours) | % Tramadol Release | Standard Deviation |
|---|---|---|
| 7.0 | 46 | 2.9 |
| 9.0 | 55 | 2.8 |
| 12.0 | 64 | 2.3 |
| 16.0 | 73 | 1.8 |
| 20.0 | 80 | 1.2 |
| 24.0 | 85 | 1.0 |

Figure 2:
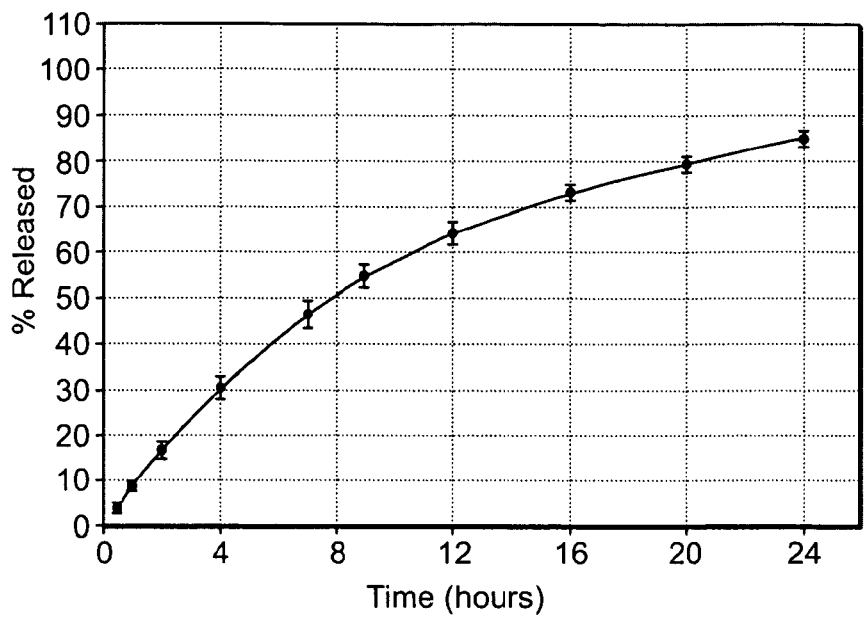
FIG. 2 is a graph showing the in vitro dissolution profile of Tramadol HCl from an intact, exemplary controlled release formulation of the invention in a U.S.P. Type I Apparatus in phosphate buffer pH 6.8.

From the release kinetics presented in FIG. 2 and summarized in Table 9, the tablets produced in Example 1, under the conditions tested, released Tramadol over 24 hours with quasi-zero order release kinetics.

In addition, the effect of alcohol on the release kinetics were studied under the same conditions as before except the extraction solvent was varied to include water, 20% ethanol in water, 40% ethanol in water, 60% ethanol in water, 80% ethanol in water and 100% ethanol. The results are set forth in FIG. 3, which shows that over 6 hours, less than about 30% of the tramadol was released when the extraction solvent contained up to 60% ethanol. The tablets performed similarly when exposed to water, 20% ethanol, 40% ethanol and 60% ethanol. However, about 50% of the tramadol was released over 6 hours when the tablets were exposed to extraction solvents containing 80% and 100% ethanol.

Figure 3:
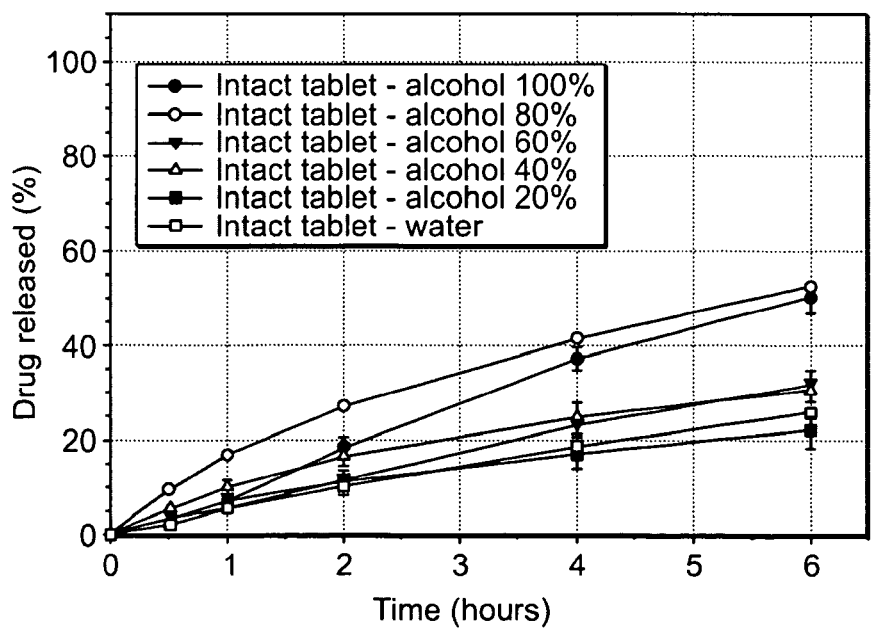
FIG. 3 is a graph showing the in vitro dissolution profile of Tramadol HCl from an intact, exemplary controlled release formulation of the invention in a U.S.P. Type I Apparatus where the solvent is water (-□-), 20% ethanol (-■-), 40% ethanol (-Δ-), 60% ethanol (-▼-), 80% ethanol (-○-) or 100% ethanol (-•-)
Figure 4:
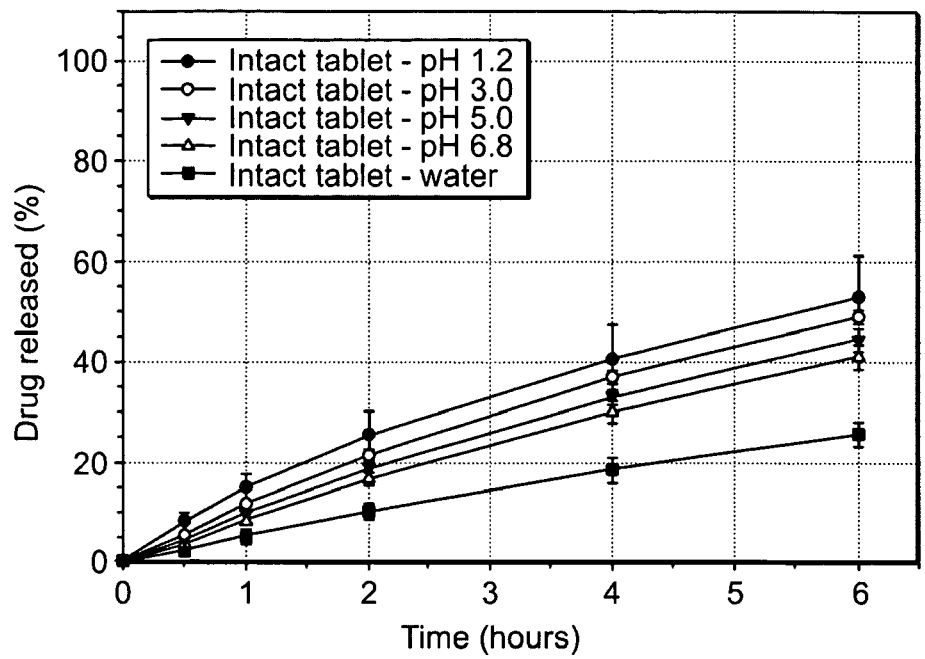
FIG. 4 is a graph showing the in vitro dissolution profile of Tramadol HCl from an intact, exemplary controlled release formulation of the invention in a U.S.P. Type I Apparatus as a function of pH where the solvent is water (-■-), buffer at pH 1.2 (-•-), buffer at pH 3.0 (-○-), buffer at pH 5.0 (-▼-), or buffer at pH 6.8 (-Δ-)

The results set forth in FIG. 3 demonstrate that the controlled release properties of the tablets produced in Example 1 was maintained in extraction solvents containing 100% water or 100% ethanol. In some cases, for example, in the presence of 20% ethanol, the release rate was even slower than in water. Furthermore, under the conditions tested, less than 20% of the Tramadol was released from the intact tablets in 30 minutes when placed in water, 20% ethanol, 40% ethanol, 60% ethanol, 80% ethanol, or 100% ethanol. Accordingly, it appears that the formulations of the invention are compatible with conventional alcoholic beverages.

In addition, the effect of pH on the release kinetics were studied under the same conditions as before except the extraction solvent was varied to include water, phosphate buffer at pH 6.8, phosphate buffer at pH 5.0, phosphate buffer at pH 3.0, and acidified water at pH 1.2. The results are set forth in FIG. 4, which shows that the controlled release properties of the tablets produced in Example 1 were maintained as pH was reduced to 1.2. It appears, however, that the rate of release increased as pH decreased from 6.8 to 1.2. Accordingly, it appears that the formulations of the invention are compatible with various common beverages (for example, carbonated drinks) that have a pH of about 3.5.

Example 3

Release Properties of Bisected Tablets

This Example demonstrates that, under the conditions tested, the tablets produced in Example 1 can be bisected without destroying the controlled release properties of the tablet. In other words, dose dumping did not occur when the tablets were broken in half.

Briefly, tablets produced in Example 1 were bisected in half. The release kinetics of the intact tablets and the halves of the bisected tablets were measured in a U.S.P. Type I Apparatus. The results were normalized for the bisected tablets and are summarized in FIG. 5. The kinetics of tramadol release from an intact tablet and a bisected tablet in a Type I Apparatus are summarized in Table 10 and Table 11, respectively.

TABLE 10

| Time (hour) | % Tramadol Release | Standard Deviation |
|---|---|---|
| 0.5 | 4 | 0.4 |
| 1.0 | 9 | 0.9 |
| 2.0 | 20 | 1.2 |
| 4.0 | 38 | 1.6 |
| 7.0 | 55 | 2.7 |
| 9.0 | 64 | 3.5 |
| 12.0 | 72 | 4.0 |
| 16.0 | 79 | 4.4 |
| 20.0 | 84 | 4.8 |
| 24.0 | 90 | 6.6 |

TABLE 11

| Time (hours) | % Tramadol Release | Standard Deviation |
|---|---|---|
| 0.5 | 9 | 1.5 |
| 1.0 | 16 | 2.4 |
| 2.0 | 29 | 3.7 |
| 4.0 | 48 | 5.6 |
| 7.0 | 68 | 7.4 |
| 9.0 | 76 | 9.5 |
| 12.0 | 88 | 7.4 |
| 16.0 | 94 | 7.8 |
| 20.0 | 98 | 8.2 |
| 24.0 | 100 | 8.5 |

Figure 5:
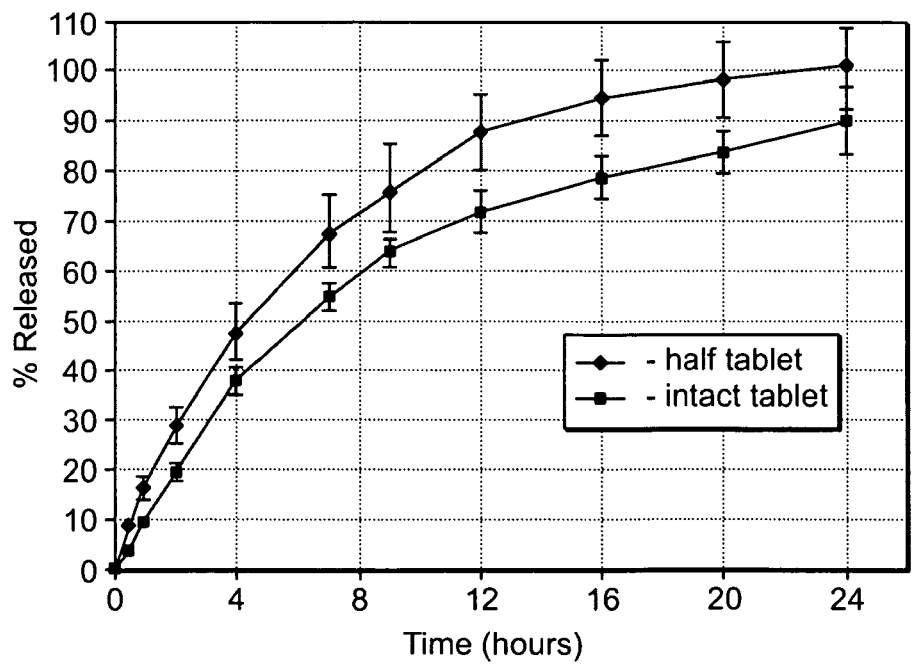
FIG. 5 is a graph showing the in vitro dissolution profile of Tramadol HCl from an intact, exemplary controlled release tablet of the invention (-•-) or from half a tablet (a bisected tablet) of the invention where the release values have been normalized relative to the intact tablet (-■-) using a U.S.P. Type I Apparatus with phosphate buffer pH 6.8.

FIG. 5 demonstrates that both the intact tablet and the bisected tablet maintain their controlled release properties and release tramadol over 20-24 hours. The release profile for the bisected tablets was similar to that of the intact tablets, however, it appeared that the bisected tablets released the tramadol slightly faster than the intact tablets. For example, at the 12 hour time point, the bisected tablet released 80-90% of the starting amount of tramadol whereas the intact tablets released 65-75% of the tramadol.

Example 4

Release Properties of Crushed Tablets

This Example describes the performance of the tablets made in Example 1 after crushing with a conventional pill crusher. In particular, the performance of the crushed tablets was measured after being exposed to a number of extraction solvents under different conditions.

Figure 6:
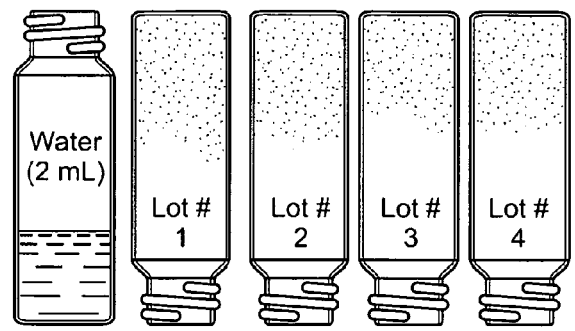
FIG. 6 is a photograph showing five vials, where the first vial contains 2 mL of water and the second through the fifth vials (inverted) contain different tablets of controlled release formulations of the invention each of which had been crushed in a pill crusher and exposed to 2 mL of water to produce a hard gel that remained at the bottom of each vial even when inverted.

Initially, the tablets produced in Example 1 were crushed with a pill crusher and combined in a glass vial with 2 mL of water (a volume typical for intravenous drug abuse and greater than the volume typically available if the crushed tablet is mixed with food). The experiment was performed using 4 different lots of tablets. Once the crushed tablet was combined with 2 mL of water, a hard gel was created within 20-30 seconds at the bottom of each leaving no available liquid that could be drawn into a syringe. As shown in FIG. 6, the vials could be inverted and the hard gels remained at the bottom of each vial. In FIG. 6, the first vial contained 2 mL of water and vials 2-5 (inverted) contained crushed tablets from four separate lots (denoted Lots 1-4) each combined with 2 mL of water. In each case, the gel produced was rigid enough to remain at the bottom of the vial even when inverted.

Figure 7:
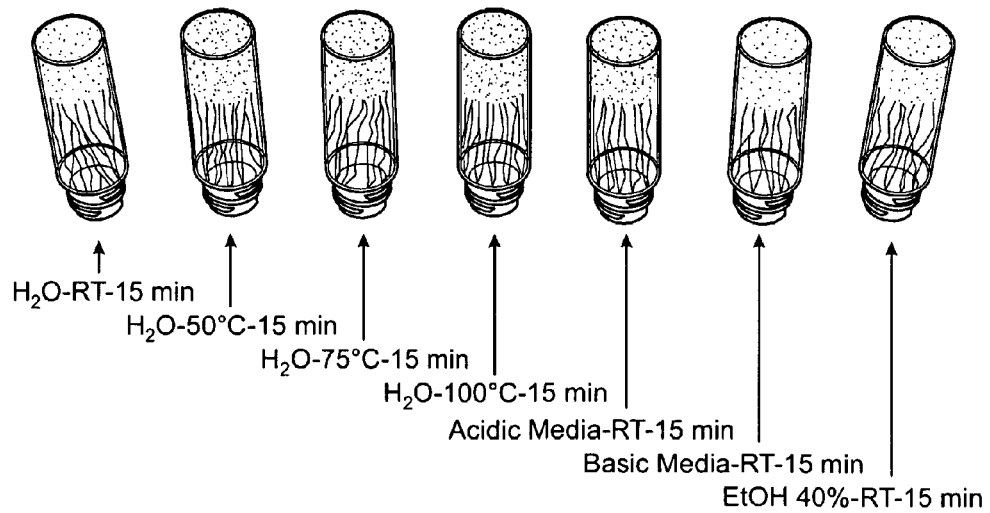
FIG. 7 is a photograph showing seven inverted vials each containing crushed tablets of the invention that had been exposed to 10 mL of (i) water at room temperature for 15 minutes with agitation (vial 1), (ii) water at 50° C. for 15 minutes with agitation (vial 2), (iii) water at 75° C. for 15 minutes with agitation (vial 3), (iv) water at 100° C. for 15 minutes with agitation (vial 4), (v) acidic media (pH 1.2) at room temperature for 15 minutes with agitation (vial 5), (vi) basic media (pH 7.5) at room temperature for 15 minutes with agitation (vial 6), and (vii) 40% ethanol in water at room temperature for 15 minutes with agitation (vial 7)

In addition, the ability to extract tramadol from the tablets produced in Example 1 was tested under different conditions after each tablet had been crushed with a pill crusher. Briefly, the crushed tablet was combined with 10 mL of extraction media (water, acid, base, or alcohol containing solvent) in a vial. The solution was heated to the specified temperature (room temperature (RT), 50° C., 75° C., or 100° C.) and agitated mechanically for 15 minutes using a wrist action Burrell agitator. It was found, however, than no residual supernatant was produced. FIG. 7 shows seven inverted vials, each containing a hard gel produced after a tablet prepared in Example 1 had been crushed in a pill crusher and exposed to 10 mL of extraction media and incubated under various conditions, which included (1) water at room temperature for 15 minutes (Vial 1, FIG. 7), (2) water at 50° C. for 15 minutes (Vial 2, FIG. 7), (3) water at 75° C. for 15 minutes (Vial 3, FIG. 7), (4) water at 100° C. for 15 minutes (Vial 4, FIG. 7), (5) acidic media (acidified water) at room temperature for 15 minutes (Vial 5, FIG. 7), (6) basic media (sodium hydroxide pH 10) at room temperature for 15 minutes (Vial 6, FIG. 7), and (7) 40% ethanol at room temperature for 15 minutes (Vial 7, FIG. 7). As can be seen in FIG. 7, all of the conditions tested resulted in formation of hard gels that remained at the bottom of each vial upon inversion. There was no residual supernatant produced by this process and so it was not possible to measure how much tramadol, if any, had been released from the formulation.

In another experiment, the release of tramadol was measured from tablets produced according to Example 1 after they had been crushed and exposed to solutions containing different concentrations of ethanol (20%, 40% and 60% ethanol). Briefly, the tablets were crushed and the amount of drug release into 900 mL of extraction media in a U.S.P. Type I Apparatus with stirring at 100 rpm at 37° C. over 30 minutes. The results are summarized in the bar chart appearing in FIG. 8. In addition, the extraction of tramadol from commercially available Ultram ER was measured once the Ultram ER had been crushed and exposed to water under the same conditions as those used for the tablets produced in Example 1.

Figure 8:
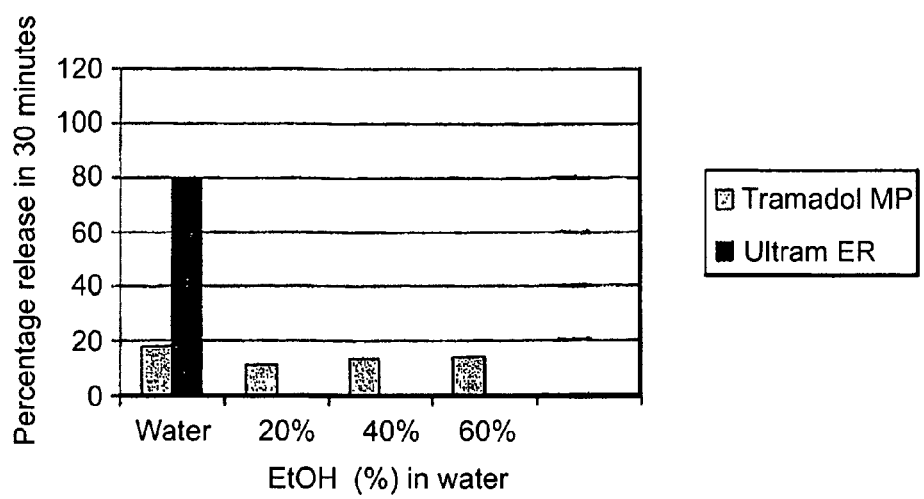
FIG. 8 is a bar chart showing the effect of different ethanol concentrations on Tramadol release from crushed tablets of the invention (bars with light shading) or Ultram ER (bar in dark shading) after incubation in 900 mL of extraction media for 30 minutes at 37° C. in a U.S.P. Type I Apparatus.

The results summarized in FIG. 8 show what there is no dose dumping of tramadol from the tablets of the invention when exposed to 900 mL of water, 20% ethanol, 40% ethanol or 60% ethanol. Under the conditions tested, less than 20% of the tramadol was released after 30 minutes. In contrast, when commercially available Ultram ER was tested under the same conditions using water as the extraction media, approximately 80% of the tramadol was released.

In another experiment, the release of tramadol was measured from tablets produced according to Example 1 after they had been crushed and exposed to extraction media having different pH values, which included water, phosphate buffer at pH 6.8, phosphate buffer at pH 5, phosphate buffer at pH 3, and acidified water at pH 1.2. The tablets were crushed and the amount of drug release into 900 mL of extraction media in a U.S.P. Type I Apparatus with stirring at 100 rpm at 37° C. over 30 minutes. The results are summarized in the bar chart appearing in FIG. 9. In addition, the extraction of tramadol from commercially available Ultram ER was measured once the Ultram ER had been crushed and exposed to water under the same conditions as those used for the tablets produced in Example 1.

Figure 9:
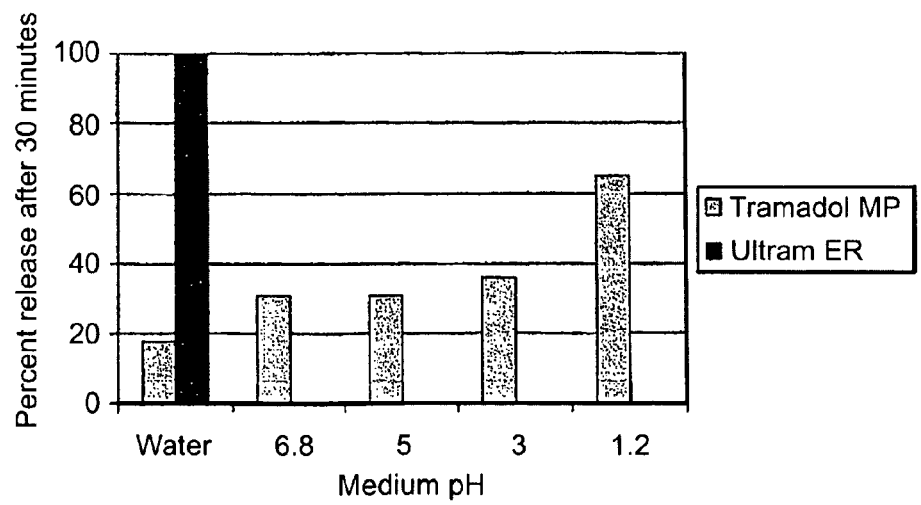
FIG. 9 is a bar chart showing the effect of pH on Tramadol release from crushed tablets of the invention (bars with light shading) or Ultram ER (bar in dark shading) after incubation in 900 mL of extraction media of various pH for 30 minutes at 37° C. in a U.S.P. Type I Apparatus.

The results summarized in FIG. 9 show that, under the conditions tested, there was no dose dumping of tramadol when incubated in 900 mL of extraction media (including water, phosphate buffer at pH 6.8, pH 5.0 or pH 3.0, and acidified water at pH 1.2). It is noted, however, that, under the conditions tested, as pH decreased the amount of released tramadol increased. For example, in water, less than 20% of the tramadol was released. In contrast, when commercially available Ultram ER was tested under the same conditions using water as the extraction media, approximately 100% of the tramadol was released. In phosphate buffer at pH 6.8, 5, and 3, approximately 30-35% of the tramadol was released from the tablets of the invention, and in acidified water at pH 1.2 approximately 65% of the tramadol was released.

Example 5

Pharmacokinetic Properties of Tramadol Tablets

The pharmacokinetic properties of the 100 mg tablets prepared in Example 1 were assessed in a single dose, randomized, crossover study in 18 healthy adults under both fasting conditions and fed conditions. After administration, plasma samples were harvested periodically, and the concentration of tramadol present in the plasma was measured via liquid chromatography-tandem mass spectrometry.

Figure 10A:
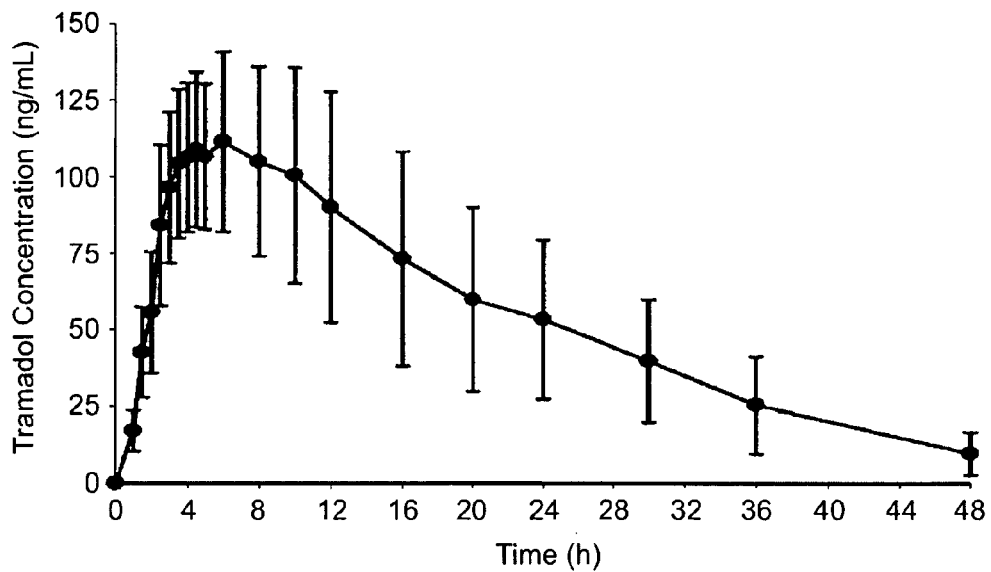
FIGS. 10A and 10B are graphs showing the mean plasma concentration of Tramadol released from an exemplary 100 mg tablet following single-dose administration to adult humans under fasting conditions (FIG. 10A) or under fed conditions (FIG. 10B)
Figure 10B:
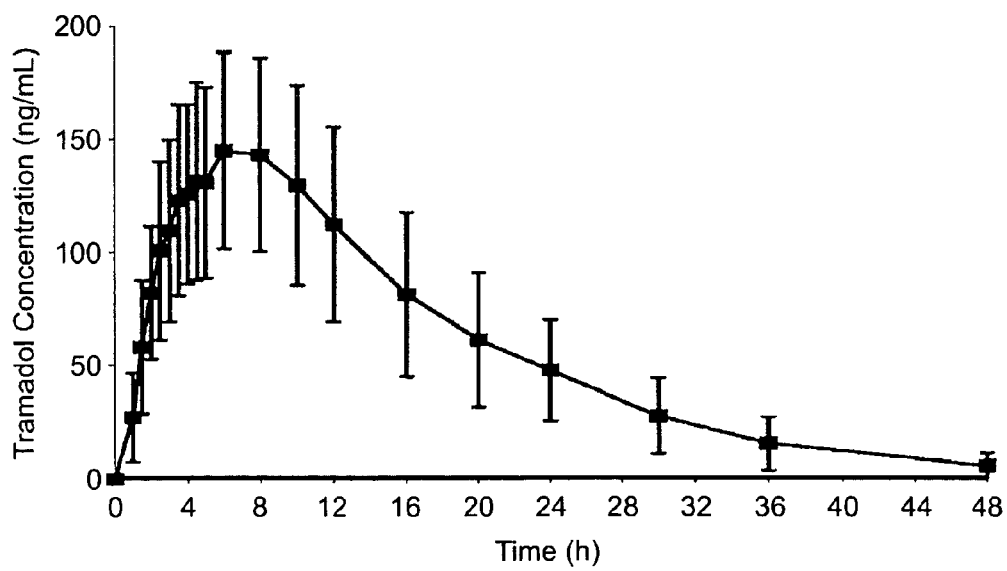

The results were plotted in FIG. 10, where the mean plasma concentrations of tramadol present in the plasma under fasting conditions is shown in FIG. 10A and the mean plasma concentrations of tramadol present in the plasma under fed conditions is shown in FIG. 10B. The median $T_{max}$ (hours) was 6.0 hours for both the fed and fasted conditions. The $C_{max}$ (ng/mL) was 120±32 ng/mL and 154±41 ng/mL under fasted and fed conditions, respectively. The $T_{1/2}$ (hours) was 8.4±2.9 hours and 6.8±2.1 hours following fasted and fed administration, respectively. The $AUC_{0-t}$ (ng·h/mL) was 2556±1026 and 2746±1057 for the fasted and fed states, respectively, and the $AUC_{0-\infty}$ (ng·h/mL) was 2703±1109 and 2829±1119 for the fasted and fed states, respectively.

Example 6

Exemplary Oxycodone Tablet

This Example describes the manufacture and testing of 40 mg oxycodone HCl tablet (BID) having a core and a controlled release coating. The coat comprises microparticles that provide controlled release properties and reduce misuse of the oxycodone disposed within the microparticles.

The microparticles were produced by extrusion spheronization, which produces the microparticles, and then were coated by fluidized bed coating. The resulting coated microparticles were blended with the coat matrix excipients and then compressed around a pre-formed polycarbophyl core.

The composition of the oxycodone containing microparticles are set forth in Table 12.

TABLE 12

| Ingredients | Mg/tablet |
| --- | --- |
| Avicel PH 101 | 72.000 |
| Contramid | 2.297 |
| Eudragit RS 30D | 9.136 |
| Triethyl citrate | 1.365 |
| Plasacryl | 0.906 |
| Oxycodone HCl | 40.000 |

The resulting microparticles then were coated in a fluid bed coater equipped with a bottom spray. The microparticles were film coated to a weight gain of 7% to 15% using an aqueous solution of Eudragid RS30C containing Plasacryl and triethyl citrate (TEC). Afterwards, a curing solution containing Opadry II White was added to provide a film around the Eudragit containing coat to reduce the likelihood of the microparticles sticking together.

The composition of the core and the coat is set forth in Table 13.

TABLE 13

| | Mg/tablet | | |
| --- | --- | --- | --- |
| Ingredients | Core blend | Coat blend | Total |
| Oxycodone HCl (provided as microparticles) | — | 125.704 | 125.704 |
| Avicel PH 101 | 13.749 | — | 13.749 |
| Contramid | — | 2.297 | 2.297 |
| Polycarbophil (Noveon AA-1) | 41.420 | — | 41.420 |
| Xanthan gum | 13.749 | 34.451 | 48.200 |
| Kollidon ® SR | — | 68.908 | 68.908 |
| Colloidal silicon dioxide | 0.349 | 1.440 | 1.789 |
| Sodium stearyl fumarate | 0.698 | 2.610 | 3.308 |
| FD&C Yellow #6 Aluminium lake | 0.035 | — | 0.035 |
| Total | 70.000 | 233.113 | 303.113 |

The dry-coated tablets were prepared using a Dry-Cota 16-Station tablet press from Manesty, UK. The core formulation was added to a first hopper in the tablet press and compressed into a core tablet. The coat formulation then was added to a second hopper in the tablet press and the core and the coat were compressed together to form the dry coated tablet. The resulting dry coated tablets then were film coated with a solution of Opadry II using a fully perforated pan coating machine (O'Hara, Mississauga, ON, CA).

Figure 11A:
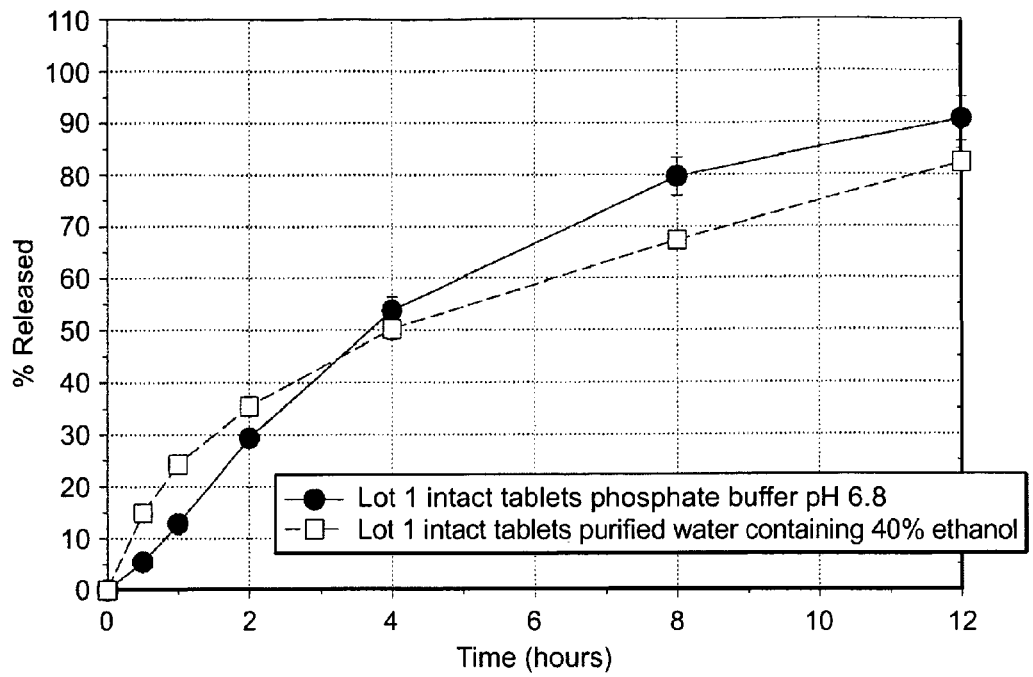
FIGS. 11A and 11B are graphs showing the in vitro dissolution profiles of an embodiment containing 40 mg oxycodone HCl in a U.S.P. Type I Apparatus at 100 rpm for twelve hours from either an intact tablet (FIG. 11A) or a crushed tablet (FIG. 11B) in phosphate buffer pH 6.8 (-•-) or buffer containing 40% ethanol (-□-)
Figure 11B:
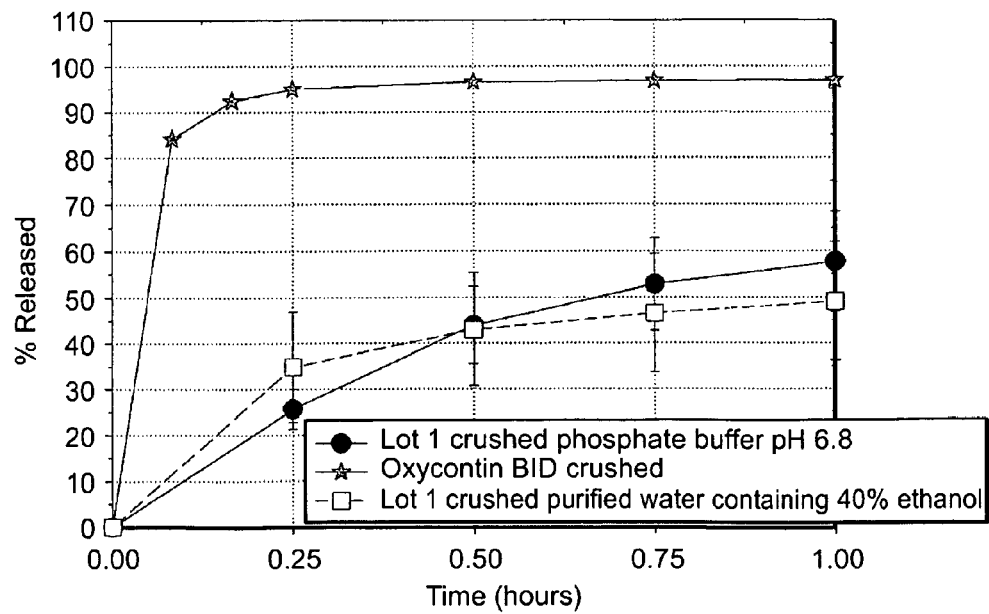
Figure 12:
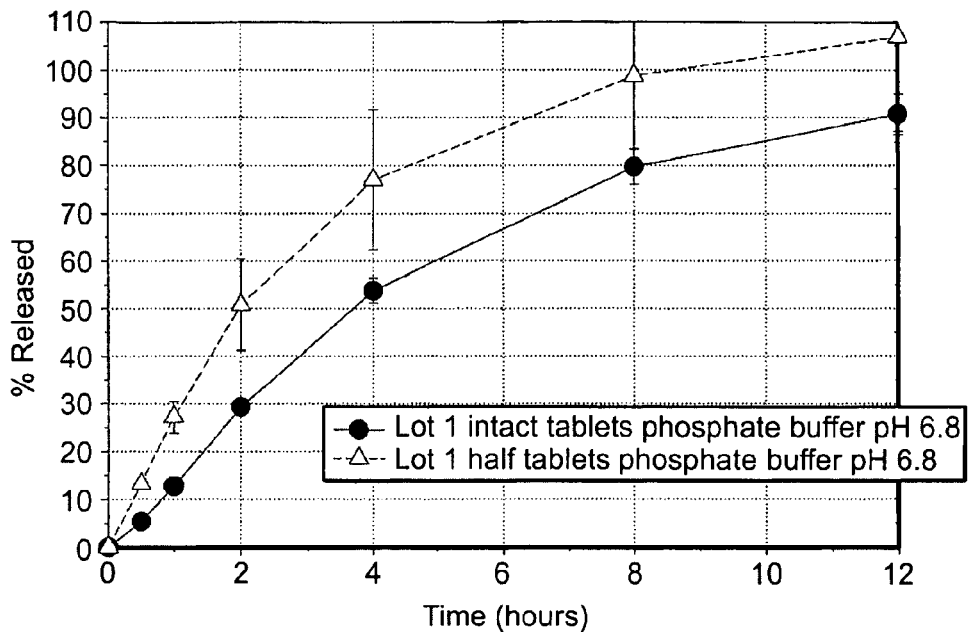
FIG. 12 is a graph showing the in vitro dissolution profiles of an embodiment containing 40 mg oxycodone HCl in a U.S.P. Type I Apparatus at 100 rpm for twelve hours from either an intact tablet in phosphate buffer pH 6.8 (-•-), or a bisected tablet in phosphate buffer pH 6.8 (-Δ-)

The in vitro release properties of the resulting tablets were measured in a U.S.P. Type I Apparatus in phosphate buffer pH 6.8 or water containing 40% ethanol. The release kinetics were measured on intact tablets (see, FIG. 11A) or crushed tablets (see, FIG. 11B), which had been crushed by using a conventional pill crusher. FIG. 11B also shows the release of oxycodone over time from Oxycontin tablets available commercially from Purdue Pharma. In addition, the release kinetics were measured for intact tablets in the presence of phosphate buffer pH 6.8, and for bisected tablets (half tablets) in the presence of phosphate buffer pH 6.8 (see, FIG. 12). As shown in FIG. 12, the release profiles were substantially the same for the intact tablets and the bisected tablets.

The intact tablets provided controlled release over 12 hours and the release was not materially affected by the presence of 40% ethanol. In contrast to the crushed Oxycontin tablets, neither the crushed nor the bisected tablets (half tablets) produced in accordance with the invention released oxycodone by dose dumping, and no dose dumping was seen in the presence of 40% ethanol.

Example 7

Exemplary Oxycodone HCl/Acetaminophen Tablet

This Example describes the manufacture and testing of a twice a day tablet (BID) containing 20 mg oxycodone HCl and 650 mg of acetaminophen. The tablet comprises a core surrounded by an enteric, controlled release coating (namely, Eudragit L30D55), where the core is in the form of a bilayer.

The composition of the microparticles is set forth in Table 14.

TABLE 14

| Ingredients | Mg/Tablet | Pellet composition (%) |
| --- | --- | --- |
| Oxycodone HCl | 20.0 | 11.51 |
| Cellulose microcrystalline (Avicel PH101) | 37.3 | 21.49 |
| Contramid | 2.7 | 1.53 |

TABLE 14-continued

| Ingredients | Mg/Tablet | Pellet composition (%) |
|---|---|---|
| Lactose monohydrate | 73.4 | 42.22 |
| Eudragit NE 30D | 20.0 | 11.51 |
| Talc | 20.0 | 11.51 |
| Colloidal silicon dioxide | 0.4 | 0.23 |
| Total | 173.8 | 100.00 |

The microparticles were produced by mixing the components set forth in Table 14 (except for the Eudragit NE 30D and Talc). The resulting mixture was subjected to extrusion and spheronization, and the resulting microparticles were coated with the Eudragit NE 30D and talc in a fluid bed coater equipped with a bottom spray. The core of the tablet was a bilayer. The oxycodone containing microparticles were incorporated in the slow release layer of the bilayer whereas the acetaminophen, as COMPAP® which was in free form and not incorporated into microparticles, was present in both the rapid release layer and the slow release layer.

The composition of the bilayer core is set forth in Table 15.

TABLE 15

| Ingredients | Tablet composition | |
|---|---|---|
| | (Mg) | (%) |
| First layer (rapid release) | | |
| COMPAP ® (which includes acetaminophen) | 288.89 | 89.72 |
| Microcrystalline Cellulose PH102 | 19.77 | 6.14 |
| Croscaramellose sodium AcDiSol | 6.70 | 2.08 |
| Colloidal silicon dioxide (Cab O sil) | 1.68 | 0.52 |
| Sodium stearyl fumarate (Pruv) | 4.83 | 1.50 |
| FD&C Yellow #6 | 0.13 | 0.04 |
| Total | 322.00 | 100.00 |
| Second layer (slow release) | | |
| Oxycodone (provided as oxycodone microparticles) | 173.79 | 24.72 |
| COMPAP ® (which includes acetaminophen) | 433.33 | 61.64 |
| Carbopol 71 G | 42.02 | 5.98 |
| Xanthan gum 80 mesh | 42.02 | 5.98 |
| Colloidal silicon dioxide (Cab O sil) | 2.95 | 0.42 |
| Sodium stearyl fumarate (Pruv) | 8.86 | 1.26 |
| Total | 703.00 | 100.00 |

The bilayer core was prepared by mixing the components of each layer and then compressing the materials in a Piccola™ bilayer tablet press (SMI Inc., NJ, USA). The bilayer tablets had a hardness in the range of 190 to 230 Newtons. The resulting bilayer core was then coated with Eudragit L30D 55 by using a fully perforated pan coating machine (O'Hara, Mississauga, ON, CA). The resulting coating contained 82 mg of Eudragit L30D 55, which accounted for 8% of the weight of the tablet.

Figure 13:
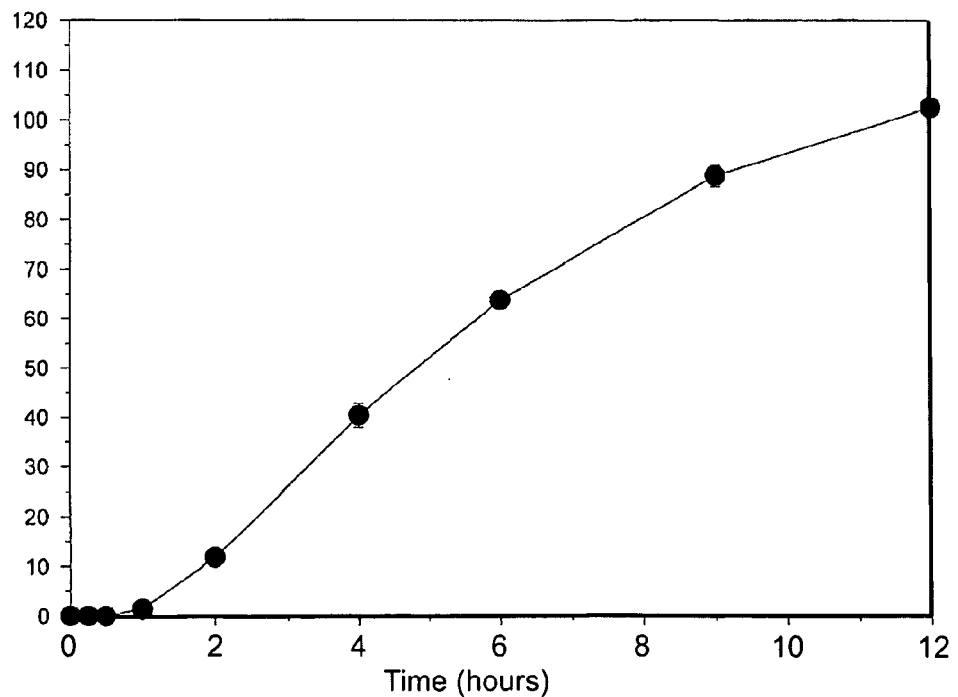
FIG. 13 is a graph showing the in vitro dissolution profile of a coated bilayer embodiment containing 20 mg oxycodone HCl/650 mg acetaminophen, where the release of oxycodone was measured in a U.S.P. Type I Apparatus at 100 rpm in acid at pH 1.2 for 1 hour and then in a phosphate buffer at pH 6.8 for 11 hours.

The in vitro release kinetics of the resulting tablet were measured in a U.S.P. Type III Apparatus at 20 dpm after incubation in 0.1M hydrochloric acid at pH 1.2 for 1 hour followed by incubation in phosphate buffer pH 6.8 for 11 hours. The results shown in FIG. 13 indicate that no oxycodone was released from the tablet for about one hour when the tablet was in 0.1M HCl. Once the pH was raised after one hour, the oxycodone was released with controlled release kinetics.

Example 8

Exemplary Once-a-Day 150 mg Tramadol Tablet

This Example describes the manufacture and testing of an exemplary once-a-day 150 mg tramadol HCl tablet, where the tablets have a monolithic core and a controlled release coating. The core comprises a super absorbent polycarbophil and the controlled release coat comprises xanthan gum and Kollidon. Tramadol containing microparticles are disposed within both the core and the coat.

The composition of the microparticles is set forth in Table 16.

TABLE 16

| Ingredients | % composition |
|---|---|
| Tramadol HCl | 57.38 |
| MCC Avicel PH 101 | 24.60 |
| Eudragit RS30D ® + Plasacryl ® + Triethyl citrate | 16.39 |
| Opadry II ® white | 1.63 |
| Total | 100.00 |

Uncoated microparticles were produced as follows. Tramadol and Avicel PH 101 were mixed in a mixer for 3 minutes under low shear conditions. The dry blend then was wetted under agitation in the same mixer by gradually adding water until a homogeneous wet mass suitable for extrusion was produced. The wet mass then was extruded at a constant speed (45 rpm) using a Laboratory Multigranulator extruder model MG-55 from LCI, Inc., NC, USA equipped with a dome die having a 0.6 mm diameter hole and a fixed extrusion gap. The extrudates then were spheronized at a constant speed (1,800 rpm) using a Marumerzier Model QJ-230T from LCI, Inc., NC, USA. The wet microparticles were dried at 45° C. in a fluid bed until a moisture content of about 2% was achieved.

A portion of the resulting microparticles were coated with an aqueous solution containing Eudragit RS 30D using a fluid bed coater. The microparticles were film coated to a weight gain of between 7% and 15%. Afterwards, a curing solution containing Opadry II White was added to provide a film around the Eudragit containing coat to reduce the likelihood of the microparticles sticking together.

The composition of the core granules is set forth in Table 17.

TABLE 17

| Ingredients | % Composition |
|---|---|
| Polycarbophilic acid (Noveon AA-1) | 80.00 |
| MCC PH-101 | 19.50 |
| Colloidal silicon dioxide | 0.25 |
| Sodium stearyl fumarate | 0.25 |
| Total | 100.00 |

In addition to the controlled release microparticles, the core contained polycarbophil as well as several other components. The remaining excipients for the core were mixed and subjected dry granulation in a roller compactor (Vector Corp.) under a roll speed of 5 rpm, a screw speed of 19 rpm, and a pressure of 800 psi. Then, uncoated microparticles were mixed with the granulated core excipients to produce the core formulation.

The composition of the coat granules is set forth in Table 18.

TABLE 18

| Ingredients | % Composition |
|---|---|
| Kollidon SR | 49.75 |
| Xanthan gum | 49.75 |
| Colloidal silicon dioxide | 0.25 |
| Sodium stearyl fumarate | 0.25 |
| Total | 100.00 |

The remaining excipients for the coat were mixed and subjected to dry granulation in a roller compactor (Vector Corp.) under a roll speed of 5 rpm, a screw speed of 19 rpm, and a pressure of 800 psi. Then, coated microparticles were mixed with the granulated coat excipients to produce the coat formulation.

The composition of the tablet is set forth in Table 19.

TABLE 19

| | Composition | |
|---|---|---|
| Ingredients | % | Mg/tablet |
| Core formulation | | |
| Tramadol HCl microparticles | 36.31 | 65.36 |
| Core granules | 62.44 | 112.39 |
| Colloidal silicon dioxide | 0.50 | 0.90 |
| Sodium stearyl fumarate | 0.75 | 1.35 |
| Total | 100 | 180 |
| Coat formulation | | |
| Tramadol HCl microparticles (film coated) | 35.98 | 196.09 |
| Coat granules | 63.02 | 343.46 |
| Colloidal silicon dioxide | 0.25 | 1.36 |
| Sodium stearyl fumarate | 0.75 | 4.09 |
| Total | 100 | 545 |

Dry-coated tablets then were prepared using a Dry-Cota 16-Station tablet press from Manesty, UK. The core formulation was added to a first hopper in the tablet press and compressed into a core tablet. The coat formulation then was added to a second hopper in the tablet press and the core and the coat were compressed together to form the dry coated tablet. The resulting dry coated tablets then were film coated with a solution of Opadry II using a fully perforated pan coating machine (O'Hara, Mississauga, ON, CA).

Figure 14A:
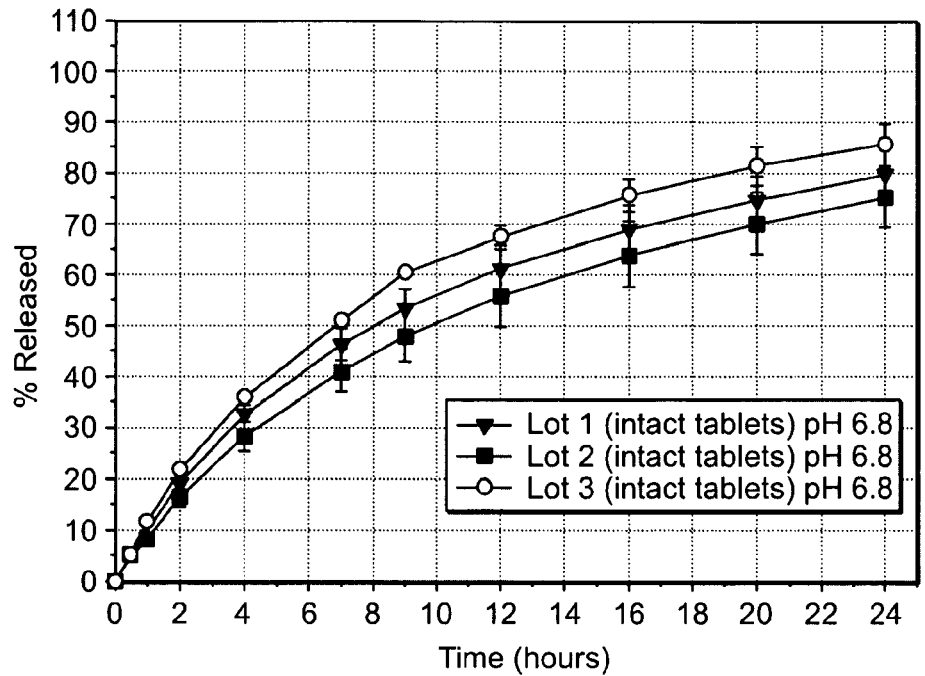
FIGS. 14A and 14B are graphs showing the in vitro dissolution profiles of an embodiment containing 150 mg Tramadol HCl in a U.S.P. Type I Apparatus at 100 rpm in phosphate buffer pH 6.8 from three different lots of intact tablets (FIG. 14A) or from crushed tablets (FIG. 14B)
Figure 14B:
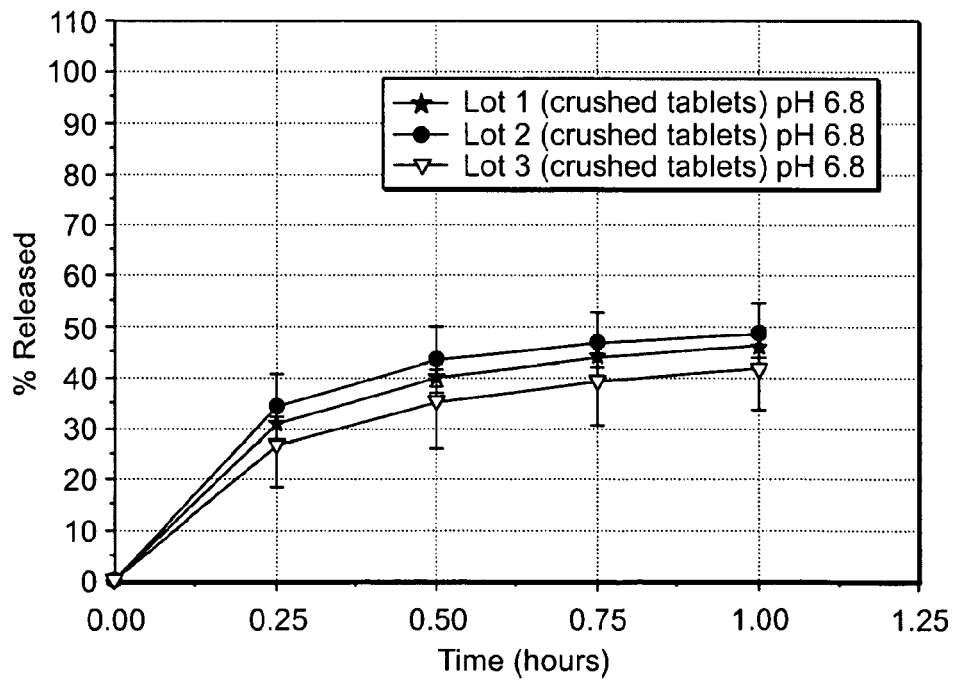

The in vitro release properties of the resulting tablets (both intact and crushed) were measured in a U.S.P. Type I Apparatus in phosphate buffer pH 6.8. Three separate batches were tested. The results of in vitro release from the intact tablets is shown in FIG. 14A and from crushed tablets is shown in FIG. 14B. The tablets were crushed using a pill crusher. The results show that the intact tablets of the invention demonstrated a controlled release of tramadol over 24 hours in phosphate buffer pH 6.8. Moreover, there was no dose dumping of tramadol from the crushed tablets when exposed to the same dissolution conditions. Under the conditions tested, less than 50% of the tramadol was released within 60 minutes.

Figure 15A:
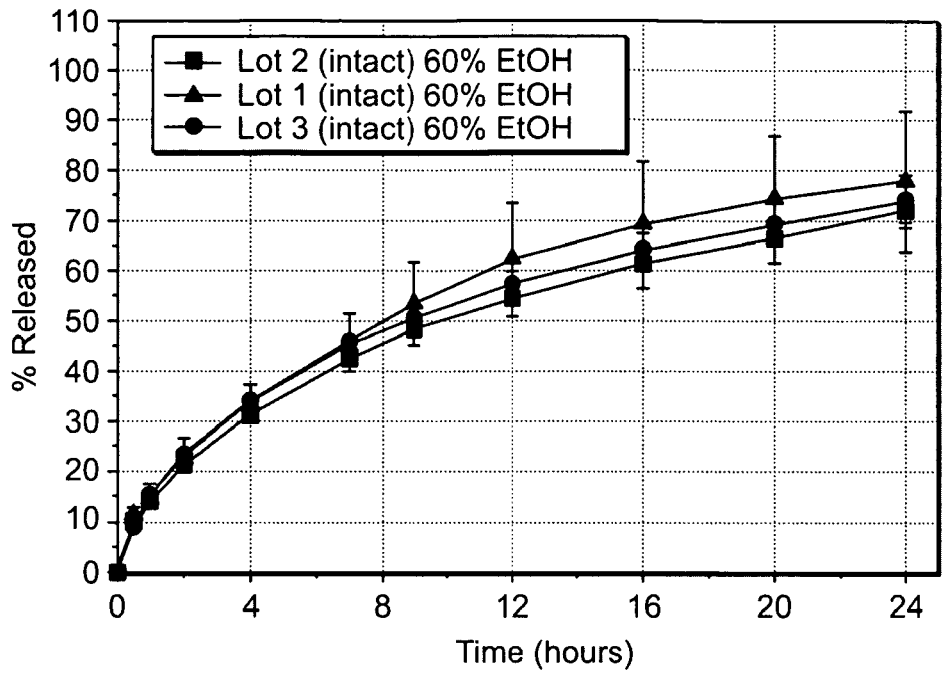
FIGS. 15A and 15B are graphs showing the in vitro dissolution profiles of an embodiment containing 150 mg Tramadol HCl in a U.S.P. Type I Apparatus at 100 rpm in water containing 60% ethanol from three different lots of intact tablets (FIG. 15A) or from crushed tablets (FIG. 15B)
Figure 15B:
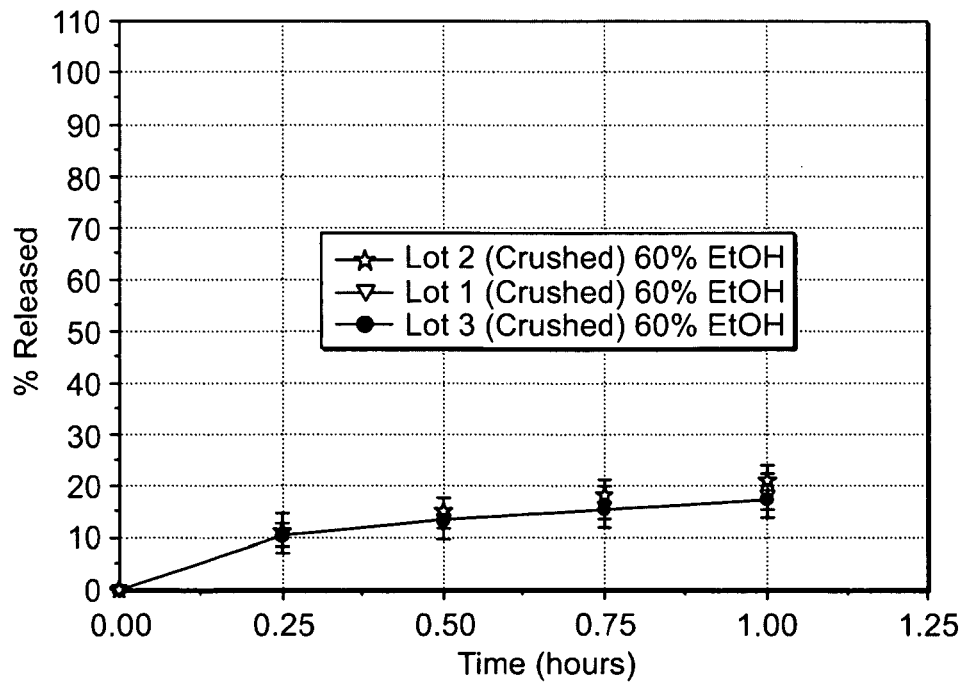

In addition, the in vitro release properties of the resulting tablets (both intact and crushed) were measured in a U.S.P. Type I Apparatus in water or water containing 20% ethanol, 40% ethanol and 60% ethanol. The same three batches were tested. The results of in vitro release from the intact tablets in water containing 60% ethanol is shown in FIG. 15A and from crushed tablets in water containing 60% ethanol is shown in FIG. 15B. Similar results were obtained when the water contained either 20% or 40% ethanol. The results show that alcohol concentrations up to at least 60% have little or no effect on the release profiles. With respect to the crushed tablets, and as shown in FIG. 15B, less than 25% of the Tramadol was released at 60 minutes in water containing 60% ethanol.

Example 9

Exemplary Once-a-Day 200 mg Tramadol Tablet

This Example describes the manufacture and testing of an exemplary once-a-day 200 mg tramadol HCl tablet, where the tablets have a monolithic core and a controlled release coating. The core comprises super absorbent polycarbophil and the controlled release coat comprises xanthan gum and Kollidon. Tramadol containing microparticles are disposed within the core and the coat.

The composition of four different lots of microparticles are set forth in Table 20.

TABLE 20

| | % composition | | | |
|---|---|---|---|---|
| Ingredients | LOT 1 | LOT 2 | LOT 3 | LOT 4 |
| Tramadol HCl | 58.3 | 57.4 | 69.6 | 69.6 |
| MCC Avicel PH 101 | 25.0 | 24.6 | 17.4 | 17.4 |
| Eudragit RS30D ® + Plasacryl ® +Triethyl citrate | 16.7 | 16.4 | 13.0 | 13.0 |
| Opadry II white | — | 1.6 | — | — |
| Total | 100.0 | 100.0 | 100.0 | 100.0 |

The formulations of uncoated microparticles were produced as follows. Tramadol and Avicel PH 101 were mixed in a mixer for 3 minutes under low shear conditions. The dry blend then was wetted under agitation in the same mixer by gradually adding water until a homogeneous wet mass suitable for extrusion was produced. The wet mass then was extruded at a constant speed (45 rpm) using a Laboratory Multigranulator extruder model MG-55 from LCI, Inc., NC, USA equipped with a dome die having a 0.6 mm diameter hole and a fixed extrusion gap. The extrudates then were spheronized at a constant speed (1,800 rpm) using a Marumerzier Model QJ-230T from LCI, Inc., NC, USA. The wet microparticles were dried at 45° C. in a fluid bed until a moisture content of about 2% was achieved.

The resulting microparticles then were coated with an aqueous solution containing Eudragit RS 30D using a fluid bed coater. The microparticles were film coated to a weight gain of between 7% and 15%. Afterwards, for Lot 2 only, a curing solution containing Opadry II White was added to provide a film around the Eudragit containing coat.

The composition of the core granules is set forth in Table 21.

TABLE 21

| Ingredients | % Composition |
|---|---|
| Polycarbophil (Noveon AA-1) | 80.00 |
| MCC PH-101 | 19.50 |

TABLE 21-continued

| Ingredients | % Composition |
|---|---|
| Colloidal silicon dioxide | 0.25 |
| Sodium stearyl fumarate | 0.25 |
| Total | 100.00 |

In addition to the controlled release microparticles, the core contained polycarbophilic acid as well as several other components. The remaining excipients for the core were mixed and subjected dry granulation in a roller compactor (Vector Corp.) under a roll speed of 5 rpm, a screw speed of 19 rpm, and a pressure of 800 psi. Then, the coated microparticles were mixed with the granulated core excipients to produce the core formulation.

The composition of the coat granules is set forth in Table 22.

TABLE 22

| Ingredients | % Composition |
|---|---|
| Kollidon SR | 33.2 |
| Xanthan gum | 66.3 |
| Colloidal silicon dioxide | 0.25 |
| Sodium stearyl fumarate | 0.25 |
| Total | 100.0 |

The remaining excipients for the coat were mixed and subjected to dry granulation in a roller compactor (Vector Corp.) under a roll speed of 5 rpm, a screw speed of 19 rpm, and a pressure of 800 psi. Then, coated microparticles were mixed with the granulated coat excipients to produce the coat formulation.

The composition of four different lots of tablets is set forth in Table 23.

Dry-coated tablets then were prepared using a Dry-Cota 16-Station tablet press from Manesty, UK. The core formulation was added to a first hopper in the tablet press and compressed into a core tablet. The coat formulation then was added to a second hopper in the tablet press and the core and the coat were compressed together to form the dry coated tablet. The resulting dry coated tablets then were film coated with a solution of Opadry II using a fully perforated pan coating machine (O'Hara, Mississauga, ON, CA).

Figure 16A:
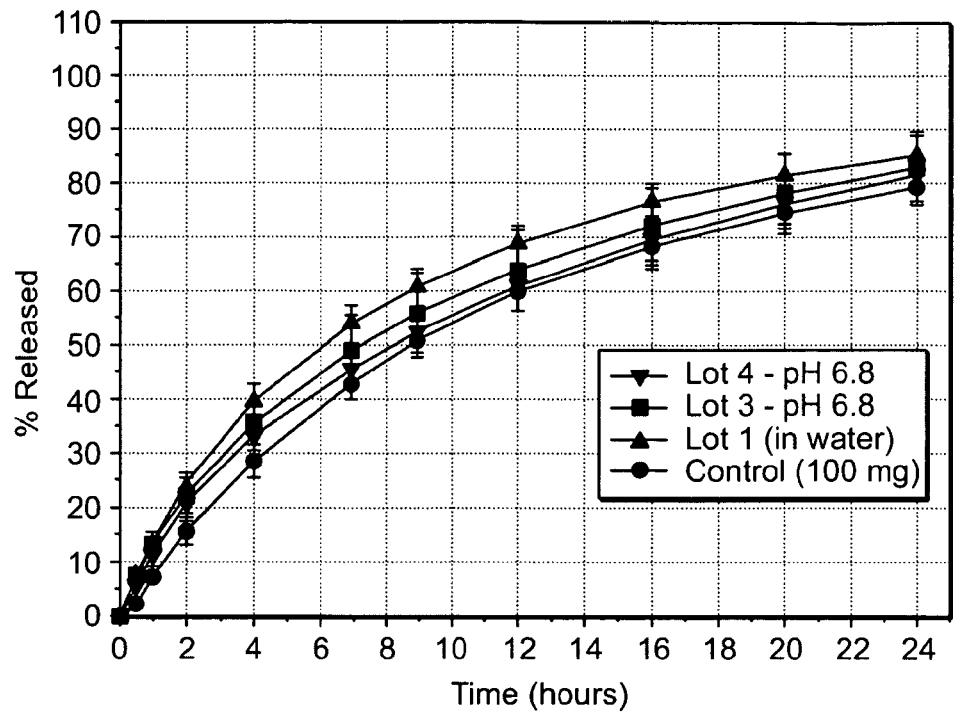
FIGS. 16A and 16B are graphs showing the in vitro dissolution profiles of an embodiment containing 200 mg Tramadol HCl in a U.S.P. Type I Apparatus at 100 rpm in phosphate buffer pH 6.8 or water from either intact tablets (FIG. 16A) or from crushed tablets (FIG. 16B)
Figure 16B:
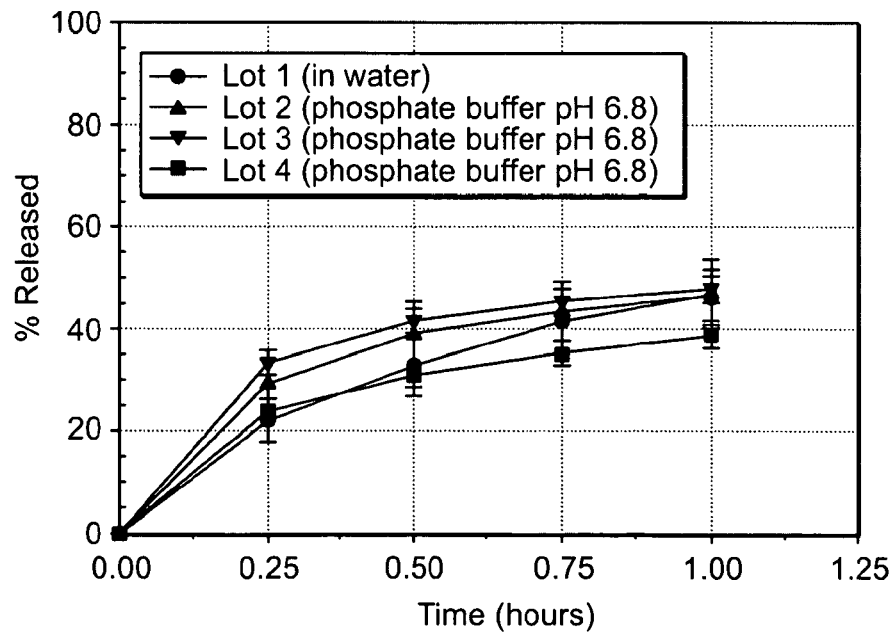

The in vitro release properties of the resulting tablets (both intact and crushed) were measured in a U.S.P. Type I Apparatus in phosphate buffer pH 6.8 or water. The results of in vitro release from intact tablets are shown in FIG. 16A and from crushed tablets is shown in FIG. 16B. The tablets were crushed using a pill crusher. The results show that the intact tablets of the invention demonstrated a controlled release of tramadol over 24 hours in phosphate buffer pH 6.8. Moreover, there was no dose dumping of tramadol from the crushed tablets when exposed to the same dissolution conditions. Under the conditions tested, less than 50% of the tramadol was released within 60 minutes.

Figure 17A:
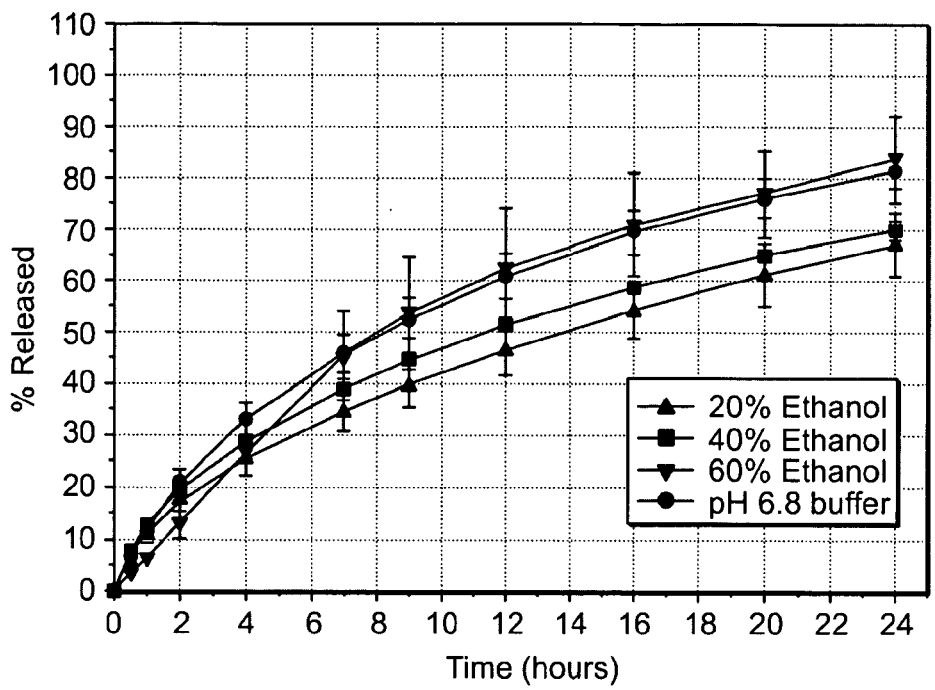
FIGS. 17A and 17B are graphs showing the in vitro dissolution profiles of an embodiment containing 200 mg Tramadol HCl in a U.S.P. Type I Apparatus at 100 rpm in phosphate buffer pH 6.8 alone (-•-) or water containing 20% ethanol (-▲-), 40% ethanol (-■A or 60% ethanol (-▼-) either from intact tablets (FIG. 17A) or from crushed tablets (FIG. 17B)
Figure 17B:
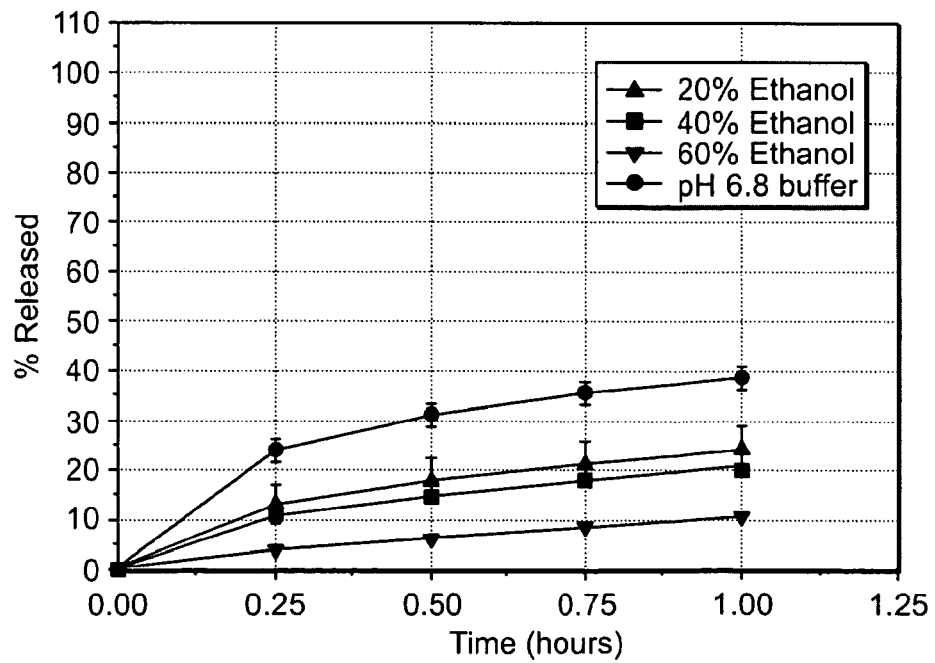

In addition, the in vitro release properties of the resulting tablets from Lot 4 (both intact and crushed) were measured in a U.S.P. Type I Apparatus in phosphate buffer pH 6.8 or water containing 20% ethanol, 40% ethanol and 60% ethanol. The results of in vitro release from the intact tablets in buffer are shown in FIG. 17A and from crushed tablets are shown in FIG. 17B. The results show that alcohol concentrations up to at least 60% have little or no effect on the release profiles. With respect to the crushed tablets, less than 15% of the tramadol was released at 60 minutes in water containing 60% ethanol.

TABLE 23

| | Lot 1 | | Lot 2 | | Lot 3 | | Lot 4 | |
|---|---|---|---|---|---|---|---|---|
| Ingredients | % | Mg/tab | % | Mg/tab | % | Mg/tab | % | Mg/tab |
| Core Compositions | | | | | | | | |
| Coated Tramadol HCl microparticles (50 mg Tramadol) | 47.62 | 85.72 | 45.87 | 87.15 | 37.84 | 71.90 | 47.92 | 71.88 |
| Core granules | 51.13 | 92.03 | 52.81 | 100.34 | 60.91 | 115.73 | 50.83 | 76.25 |
| Colloidal silicon dioxide | 0.50 | 0.90 | 0.50 | 0.95 | 0.50 | 0.95 | 0.50 | 0.75 |
| Sodium stearyl fumarate | 0.75 | 1.35 | 0.75 | 1.43 | 0.75 | 1.43 | 0.75 | 1.13 |
| Total Core | 100 | 180 | 100 | 190 | 100 | 190 | 100 | 150 |
| Coat Compositions | | | | | | | | |
| Coated Tramadol HCl microparticles (150 mg Tramadol) | 47.18 | 257.13 | 46.68 | 261.41 | 38.50 | 215.60 | 35.94 | 215.64 |
| Coat granules | 51.82 | 282.42 | 52.32 | 292.99 | 52.15 | 292.04 | 63.06 | 378.36 |
| Xanthan gum | — | — | — | — | 8.35 | 46.76 | — | — |
| Colloidal silicon dioxide | 0.25 | 1.36 | 0.25 | 1.40 | 0.25 | 1.40 | 0.25 | 1.50 |
| Sodium stearyl fumarate | 0.75 | 4.09 | 0.75 | 4.20 | 0.75 | 4.20 | 0.75 | 4.50 |
| Total Coat | 100 | 545 | 100 | 560 | 100 | 560 | 100 | 600 |
| Tablet Weight | | 725 | | 750 | | 750 | | 750 |

Example 10

Exemplary Twelve Hour 30 mg Hydrocodone Bitartrate Tablet

This Example describes the manufacture and testing of an exemplary twelve hour tablet containing 30 mg of Hydrocodone bitartrate. The tablets have a monolithic core and a controlled release coating. The core comprises super absorbent polycarbophil and the controlled release coat comprises xanthan gum and Kollidon. Hydrocodone containing microparticles are disposed within the coat. No active ingredient was disposed within the core.

The composition of the hydrocodone containing microparticles is set forth in Table 24.

TABLE 24

| Ingredients | % Composition |
| --- | --- |
| Hydrocodone bitartrate | 31.82 |
| MCC Avicel PH 101 | 59.09 |
| Eudragit RS30D ® + Plasacryl ® +Triethyl citrate | 9.09 |
| Total | 100.00 |

The microparticles were produced as follows. Hydrocodone bitartrate and Avicel PH 101 were mixed in a mixer for 3 minutes under low shear conditions. The dry blend then was wetted under agitation in the same mixer by gradually adding water until a homogeneous wet mass suitable for extrusion was produced. The wet mass then was extruded at a constant speed (45 rpm) using a Laboratory Multigranulator extruder model MG-55 from LCI, Inc., NC, USA equipped with a dome die having a 0.6 mm diameter hole and a fixed extrusion gap. The extrudes then were spheronized at a constant speed (1,800 rpm) using a Marumerzier Model QJ-230T from LCI, Inc., NC, USA. The wet microparticles were dried at 45° C. in a fluid bed until a moisture content of about 2% was achieved.

The resulting microparticles were coated with an aqueous solution containing Eudragit RS 30D using a fluid bed coater. The microparticles were film coated to a weight gain of between 7% and 15%.

The composition of the core granules is set forth in Table 25.

TABLE 25

| Ingredients | % Composition |
| --- | --- |
| Polycarbophil (Noveon AA-1) | 80.00 |
| MCC PH-101 | 19.50 |
| Colloidal silicon dioxide | 0.25 |
| Sodium stearyl fumarate | 0.25 |
| Total | 100.00 |

The core contained polycarbophil as well as several other components. These excipients were mixed and subjected dry granulation in a roller compactor (Vector Corp.) under a roll speed of 5 rpm, a screw speed of 19 rpm, and a pressure of 800 psi.

The composition of the coat granules is set forth in Table 26.

TABLE 26

| Ingredients | % Composition |
| --- | --- |
| Kollidon SR | 33.17 |
| Xanthan gum | 66.33 |
| Colloidal silicon dioxide | 0.25 |
| Sodium stearyl fumarate | 0.25 |
| Total | 100.00 |

The remaining excipients for the coat were mixed and subjected to dry granulation in a roller compactor (Vector Corp.) under a roll speed of 5 rpm, a screw speed of 19 rpm, and a pressure of 800 psi. Then, the microparticles were mixed with the granulated coat excipients to produce the coat formulation.

The composition of intact tablets is set forth in Table 27.

Table 27

| | Composition | |
| --- | --- | --- |
| Ingredients | % | Mg/tab |
| Core Formulation | | |
| Hydrocodone bitartrate microparticles | — | — |
| Core granules | 45.80 | 77.86 |
| Klucel HF | 52.95 | 90.02 |
| Colloidal silicon dioxide | 0.50 | 0.85 |
| Sodium stearyl fumarate | 0.75 | 1.28 |
| Total | 100.00 | 170.00 |
| Coat Formulation | | |
| Hydrocodone bitartrate microparticles | 21.93 | 94.30 |
| Coat granules | 53.81 | 231.38 |
| Avicel PH 102 | 23.26 | 100.02 |
| Colloidal silicon dioxide | 0.25 | 1.08 |
| Sodium stearyl fumarate | 0.75 | 3.23 |
| Total | 100.00 | 430.00 |

Dry-coated tablets then were prepared using a Dry-Cota 16-Station tablet press from Manesty, UK. The core formulation was added to a first hopper in the tablet press and compressed into a core tablet. The coat formulation then was added to a second hopper in the tablet press and the core and the coat were compressed together to form the dry coated tablet. The resulting dry coated tablets then were film coated with a solution of Opadry II using a fully perforated pan coating machine (O'Hara, Mississauga, ON, CA).

Figure 18A:
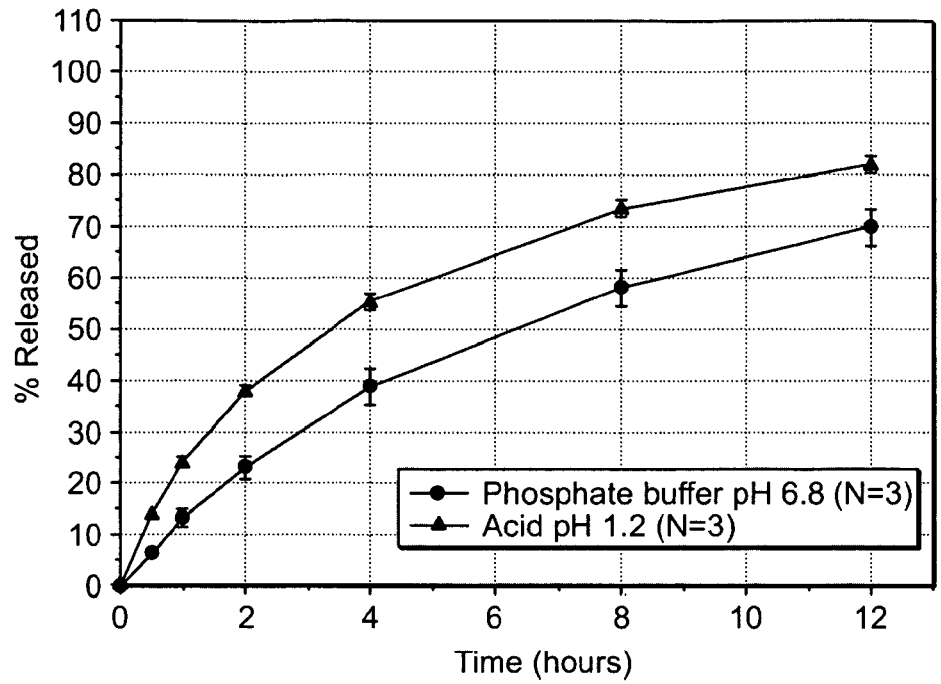
FIGS. 18A and 18B are graphs showing the in vitro dissolution profiles of an embodiment containing 30 mg hydrocodone in a U.S.P. Type I Apparatus at 100 rpm in phosphate buffer pH 6.8 (-•-) or acid pH 1.2 (-▲-) either from intact tablets (FIG. 18A) or from crushed tablets (FIG. 18B).
Figure 18B:
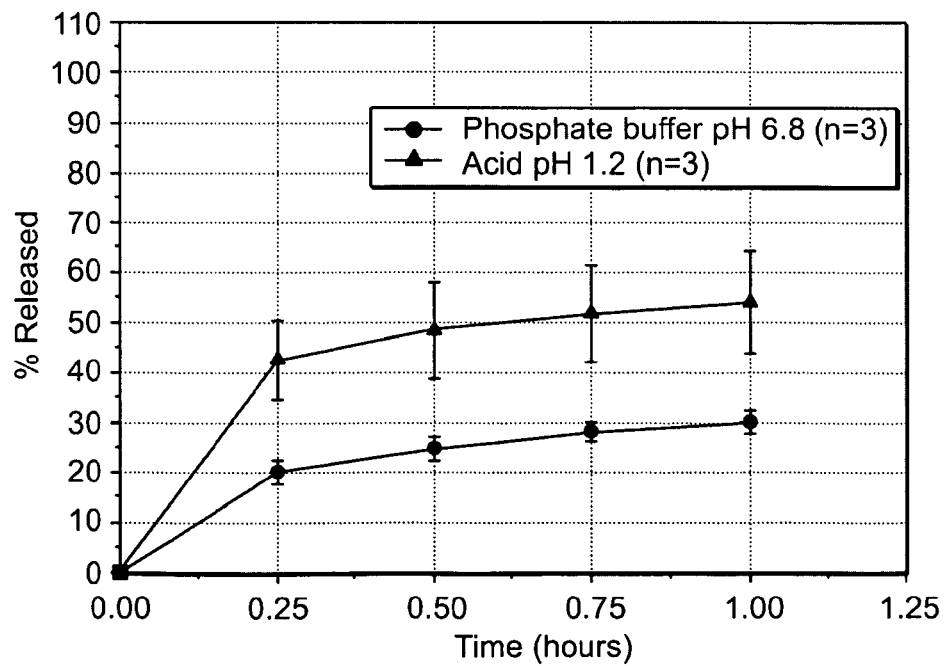

The in vitro release properties of the resulting tablets (both intact and crushed) were measured in a U.S.P. Type I Apparatus in phosphate buffer pH 6.8 or 0.1M hydrochloric acid pH 1.2. The results of in vitro release from the intact tablets are shown in FIG. 18A and from crushed tablets are shown in FIG. 18B. The tablets were crushed by using a pill crusher. The results show that the intact tablets demonstrated a controlled release of Hydrocodone bitartrate over 12 hours in phosphate buffer pH 6.8 and in acid pH 1.2. However, the drug release rate in the acid was slightly higher than the release in phosphate buffer pH 6.8. Furthermore, there was no dose dumping of hydrocodone bitartrate from the crushed tablets when exposed to the same dissolution conditions. Under the conditions tested, less than 30%, and 55% of hydrocodone was released within 60 minutes in phosphate buffer pH 6.8 and in acid pH 1.2, respectively.

INCORPORATION BY REFERENCE

The entire disclosure of each of the patent and scientific documents referred to herein is incorporated by reference for all purposes.

EQUIVALENTS

Although the present invention has been illustrated by means of preferred embodiments thereof, it is understood that the invention intends to cover broad aspects thereof without departing from the spirit and scope of the invention as defined in the appended claims.

What is claimed is:

1. A solid, compressed controlled release formulation, comprising:
   (a) a core comprising a superabsorbent material comprising a cross-linked acrylic acid polymer characterized in that 1 gram of the cross-linked acrylic acid polymer absorbs at least 30 mL of water, the superabsorbent material comprising from 30% to 70% (w/w) of the core;
   (b) a controlled release coat surrounding the core; and
   (c) a plurality of controlled release microparticles having a pharmaceutically active agent disposed therein, wherein the microparticles are disposed within the core, the coat, or both the core and the coat, the formulation having a hardness from about 200 N to about 400 N, and wherein the formulation
      (i) when intact and exposed to an aqueous medium, the pharmaceutically active agent is released from the formulation over a prolonged period of time,
      (ii) when crushed to break the controlled release coat and expose the core, and exposed to a volume of an aqueous medium that weighs 30 times the weight of the superabsorbent material in the formulation, the formulation absorbs all of the aqueous medium and swells to create a hard gel that traps the microparticles, and the microparticles provide controlled release of the pharmaceutically active agent, and
      (iii) when broken and exposed to 900 mL of water in a U.S.P. Type I Apparatus with stirring at 100 rpm for 30 minutes at 37° C., less than about 50% by weight of the pharmaceutically active agent originally present in the formulation before it was broken is released into the water.

2. The formulation of claim 1, wherein the microparticles are disposed within the core.

3. The formulation of claim 1, wherein the microparticles are disposed within the coat.

4. The formulation of claim 1, wherein the microparticles are disposed within both the core and the coat.

5. The formulation of claim 1, wherein the core is monolithic.

6. The formulation of claim 1, wherein the core comprises a first layer, a second layer and an optional third layer.

7. The formulation of claim 6, wherein the first layer comprises the microparticles.

8. The formulation of claim 1, wherein the pharmaceutically active agent is released over a period of at least 12 hours.

9. The formulation of claim 1, wherein the pharmaceutically active agent is released over a period of at least 24 hours.

10. The formulation of claim 1, wherein the superabsorbent material is present at about 30% to about 50% (w/w) of the core.

11. The formulation of claim 1, wherein the core further comprises a granulating agent.

12. The formulation of claim 11, wherein the granulating agent is selected from the group consisting of xanthan gum, polyethylene oxide, polyvinylpyrrolidone, cellulose and sucrose derivatives, and mixtures thereof.

13. The formulation of claim 1, wherein the coat comprises a controlled release agent.

14. The formulation of claim 13, wherein the controlled release agent is selected from the group consisting of acetate succinate, a polyvinyl derivative, polyethylene oxide, polyacrylic acid, modified starch, cross-linked high amylose starch, hydroxypropyl starch, hydroxypropyl methylcellulose phthalate, cellulose, microcrystalline cellulose, carboxymethylethyl cellulose, cellulose acetate, methylcellulose, ethylcellulose, hydroxypropyl cellulose, hydroxypropylmethyl cellulose, cellulose phthalate, cellulose acetate, cellulose acetate phthalate, cellulose acetate propionate, cellulose acetate succinate, cellulose acetate butyrate, cellulose acetate trimellitate, poloxamer, povidone, alginic acid, sodium alginate, polyethylene glycol, polyethylene glycol alginate, gums, polymethacrylate, a copolymer of methacrylic acid and ethyl acrylate, a copolymer of polymethyl vinyl ether and malonic acid anhydride, a copolymer of polymethyl vinyl ether and malonic acid or the ethyl-, isopropyl-, n-butylesters thereof, zein, and mixtures of any of the foregoing.

15. The formulation of claim 13, wherein the coat further comprises a viscosity-increasing agent.

16. The formulation of claim 15, wherein the viscosity increasing agent is selected from the group consisting of xanthan gum, polyethylene oxide, polyvinylpyrrolidone, cellulose and a sucrose derivative.

17. The formulation of claim 1, wherein the microparticles comprise a controlled release agent.

18. The formulation of claim 17, wherein the controlled release agent is selected from the group consisting of acetate succinate, polyvinyl derivatives, polyethylene oxide, polyacrylic acid, modified starch, cross-linked high amylose starch, hydroxypropyl starch, hydroxypropyl methylcellulose phthalate, cellulose, microcrystalline cellulose, carboxymethylethyl cellulose, cellulose acetate, methylcellulose, ethylcellulose, hydroxypropyl cellulose, hydroxypropylmethyl cellulose, cellulose phthalate, cellulose acetate, cellulose acetate phthalate, cellulose acetate propionate, cellulose acetate succinate, cellulose acetate butyrate, cellulose acetate trimellitate, poloxamer, povidone, alginic acid, sodium alginate, polyethylene glycol, polyethylene glycol alginate, gums, polymethacrylate, a copolymer of methacrylic acid and ethyl acrylate, a copolymer of polymethyl vinyl ether and malonic acid anhydride, a copolymer of polymethyl vinyl ether and malonic acid or the ethyl-, isopropyl-, n-butylesters thereof, zein, and mixtures of any of the foregoing.

19. The formulation of claim 1, wherein the microparticles are coated with a controlled release coat.

20. The formulation of claim 19, wherein the controlled release coat is selected from the group consisting of polymethacrylate, cellulose, a cellulose derivative, polyvinyl acetate, polyvinyl pyrollidone, and mixtures thereof.

21. The formulation of claim 20, wherein the cellulose derivative is selected from the group consisting of ethyl cellulose and hydroxypropyl cellulose.

22. The formulation of claim 20, wherein the polymethacrylate comprises a polymeric mixture of ethyl acrylate, methyl methacrylate and trimethylammonioethyl methacrylate.

23. The formulation of claim 1, wherein the microparticles have an average diameter in the range of from about 1 μm to about 1000 μm, from about 200 μm to about 900 μm, or from about 300 μm to about 800 μm.

24. The formulation of claim 23, wherein the microparticles have an average diameter of about 700 μm.

25. The formulation of claim 23, wherein the microparticles have an average diameter in the range of from about 1 μm to about 400 μm, from about 5 μm to about 300 μm, or from about 10 μm to about 200 μm.

26. The formulation of claim 25, wherein the microparticles have an average diameter of about 100 μm.

27. The formulation of claim 1, wherein, in element (iii), less than about 25% by weight of the pharmaceutically active agent originally present in the formulation before it was broken is released into the water.

28. The formulation of claim 1, wherein, when the formulation is broken and exposed to 900 mL of an aqueous solution containing 60% (v/v) ethanol in a U.S.P. Type 1 Apparatus with stirring at 100 rpm for 30 minutes at 37° C., less than about 50% by weight of the pharmaceutically active agent originally present in the formulation before it was broken is released into the aqueous solution.

29. The formulation of claim 28, wherein less than about 25% by weight of the pharmaceutically active agent originally present in the formulation before it was broken is released into the aqueous solution.

30. The formulation of claim 1, wherein the formulation is in the form of a capsule, caplet, pill, or a compressed tablet.

31. The formulation of claim 1, wherein the pharmaceutically active agent is a drug capable of abuse.

32. The formulation of claim 31, wherein the drug is an opioid analgesic, hypnotic agent, anxiolytic, or a respiratory stimulant.

33. A method of providing controlled release of a pharmaceutically active agent, the method comprising orally administering to an individual in need of the pharmaceutically active agent the controlled release formulation of claim 1.

34. The formulation of claim 1, wherein the formulation, when crushed to break the controlled release coat and expose the core and exposed to 2 mL of an aqueous medium, the formulation absorbs all of the aqueous medium and swells to create a hard gel that traps the microparticles.

35. The formulation of claim 1, wherein the formulation, when crushed to break the controlled release coat and expose the core and exposed to 10 mL of an aqueous medium, the formulation absorbs all of the aqueous medium and swells to create a hard gel that traps the microparticles.

36. The formulation of claim 1, wherein the cross-linked acrylic acid polymer is a copolymer.

37. The formulation of claim 1, wherein the cross-linked acrylic acid polymer is selected from the group consisting of an acrylic acid polymer cross-linked with divinyl glycol, an acrylic acid polymer cross-linked with allyl ethers of pentaerythritol, and a mixture thereof.

38. The formulation of claim 1, wherein the cross-linked acrylic acid polymer is polycarbophil.

39. The formulation of claim 1, wherein the cross-linked acrylic acid polymer is polycarbophilic calcium.

40. The formulation of claim 1, wherein the cross-linked acrylic acid polymer is a carbomer homopolymer type A.

41. The formulation of claim 1, wherein the cross-linked acrylic acid polymer is a carbomer homopolymer type B.

42. The formulation of claim 1, wherein 1 gram of the cross-linked acrylic acid polymer absorbs at least 50 mL of water.

* * * * *